(12) United States Patent
Nakauchi et al.

(10) Patent No.: US 11,856,927 B2
(45) Date of Patent: Jan. 2, 2024

(54) FINDING AND TREATMENT OF INFLAMMATION AFTER BIRTH IN CHIMERIC ANIMAL

(71) Applicant: The University of Tokyo, Tokyo (JP)

(72) Inventors: Hiromitsu Nakauchi, Tokyo (JP); Tomoyuki Yamaguchi, Tokyo (JP); Sanae Hamanaka, Tokyo (JP); Hideyuki Sato, Tokyo (JP); Hideki Masaki, Tokyo (JP); Naoaki Mizuno, Tokyo (JP); Motoo Watanabe, Tokyo (JP)

(73) Assignee: The University of Tokyo, Tokyo (JP)

( * ) Notice: Subject to any disclaimer, the term of this patent is extended or adjusted under 35 U.S.C. 154(b) by 1078 days.

(21) Appl. No.: 16/480,169

(22) PCT Filed: Jan. 25, 2018

(86) PCT No.: PCT/JP2018/002178
§ 371 (c)(1),
(2) Date: Oct. 17, 2019

(87) PCT Pub. No.: WO2018/139502
PCT Pub. Date: Aug. 2, 2018

(65) Prior Publication Data
US 2020/0137991 A1  May 7, 2020

(30) Foreign Application Priority Data
Jan. 25, 2017 (JP) .................................. 2017-011349

(51) Int. Cl.
*A01K 67/027* (2006.01)
*A61P 37/06* (2006.01)
*A61K 31/573* (2006.01)
*C12N 15/09* (2006.01)

(52) U.S. Cl.
CPC ........ *A01K 67/0271* (2013.01); *A61K 31/573* (2013.01); *A61P 37/06* (2018.01); *A01K 2217/05* (2013.01); *A01K 2217/075* (2013.01); *A01K 2227/105* (2013.01); *A01K 2267/035* (2013.01); *C12N 15/09* (2013.01)

(58) Field of Classification Search
None
See application file for complete search history.

(56) References Cited

U.S. PATENT DOCUMENTS

| | | |
|---|---|---|
| 2004/0208857 A1 | 10/2004 | Bader et al. |
| 2009/0313710 A1 | 12/2009 | Mukaidani et al. |
| 2011/0258715 A1 | 10/2011 | Nakauchi et al. |
| 2011/0283374 A1 | 11/2011 | Nakauchi et al. |
| 2020/0008404 A1 | 1/2020 | Nakauchi et al. |

FOREIGN PATENT DOCUMENTS

| | | |
|---|---|---|
| JP | 2004-519437 A | 7/2004 |
| JP | 2016-154555 A | 9/2016 |
| JP | 2016-195605 A | 11/2016 |
| WO | WO-2008/001614 A1 | 1/2008 |
| WO | WO-2010/021390 A1 | 2/2010 |
| WO | WO-2010/087459 A1 | 8/2010 |
| WO | WO-2015/155904 A1 | 10/2015 |

OTHER PUBLICATIONS

Tamir et al. Cell Stem Cell No. 15, pp. 406-409, Oct. 2, 2014 (Year: 2014).*
Tamir Rashid et al. Cell Stem Cell No. 15, pp. 406-409, Oct. 2, 2014, (Year: 2014).*
Kobayashi et al. Cell 142, 787-799 , 2010 (Year: 2010).*
Office Action dated Jan. 25, 2022, for Japanese Application No. 2021-003596, Nakauchi et al., "Finding and Treatment of Inflammation after Birth in Chimeric Animal," filed Jan. 13, 2021 (6 pages).
Office Action dated May 26, 2020 for Japanese Patent Application No. 2018-564608, Nakauchi et al., "Finding and Treatment of Inflammation After Birth in Chimeric Animal," filed Jan. 25, 2018 (4 pages).
Official Communication dated Oct. 6, 2020 for Japanese Patent Application No. 2018-564608, Nakauchi et al., "Finding and Treatment of Inflammation after Birth in Chimeric Animal," filed Jan. 25, 2018 (3 pages).
Chen et al., "RAG-2-deficient blastocyst complementation: an assay of gene function in lymphocyte development," Proc Natl Acad Sci USA. 90(10):4528-32 (1993).
International Search Report dated Mar. 6, 2018 for International Patent Application No. PCT/JP2018/002178, Nakauchi et al., "Finding and Treatment of Inflammation after Birth in Chimeric Animal," filed Jan. 25, 2018 (10 pages).
Kobayashi et al., "Generation of rat pancreas in mouse by interspecific blastocyst injection of pluripotent stem cells," Cell. 142(5):787-99 (2010).
Kobayashi et al., "From cell therapy to organ regeneration therapy: generation of functional organs for pluripotent stem cells," Japanese Journal of Clinical Medicine. 69(12):2148-55 (2011) (20 pages).
Okada, "Development of highly immunodeficient mice and application thereof to biomedical research," Cytometry Research. 27(1):25-31 (2017) (25 pages).
Rashid et al., "Revisiting the flight of Icarus: making human organs from PSCs with large animal chimeras," Cell Stem Cell. 15(4):406-409 (2014).

(Continued)

*Primary Examiner* — Jana A Hines
*Assistant Examiner* — Khatol S Shahnan Shah
(74) *Attorney, Agent, or Firm* — Clark & Elbing LLP; Susan M. Michaud

(57) ABSTRACT

The present invention has found that chimeric animals suffer from noticeable inflammation after birth, though neither immune response nor inflammation in the fetal period of these animals has been reported hitherto. This is an unexpected finding since chimeric animals in the fetal period were exclusively analyzed in prior studies and thus it is deemed that immunotolerance has been theoretically established therein. The present invention provides a composition for suppressing immune response or inflammation in the fetal period of a born chimeric animal.

12 Claims, 12 Drawing Sheets

Specification includes a Sequence Listing.

(56) References Cited

OTHER PUBLICATIONS

Sugitani et al., "Evaluation of pancreatic endocrine function during early phase following simultaneous pancreas-kidney transplantation in three Japanese cases conducted after the enactment of the organ transplantation law," Tounyobyo. 46(3):217-227 (2003) (29 pages).
Walsh et al., "Humanized mouse models of clinical disease," Annu Rev Pathol. 12:187-215 (2017).
Wu et al., "Interspecies chimerism with mammalian pluripotent stem cells," Cell. 168(3):473-86 (2017) (29 pages).
Yamaguchi et al., "Interspecies organogenesis generates autologous functional islets," Nature. 542(7640):191-6 (2017) (15 pages).
Billingham et al., "Actively acquired tolerance of foreign cells," Nature 172(4379):603-606 (1953).
Fehilly et al., "Interspecific chimaerism between sheep and goat," Nature 307(5952):634-636 (1984).
Gustafson et al., "Tolerance of sheep-goat chimeras to their component cells," J Reprod Immunol. 23(2):155-168 (1993).

\* cited by examiner

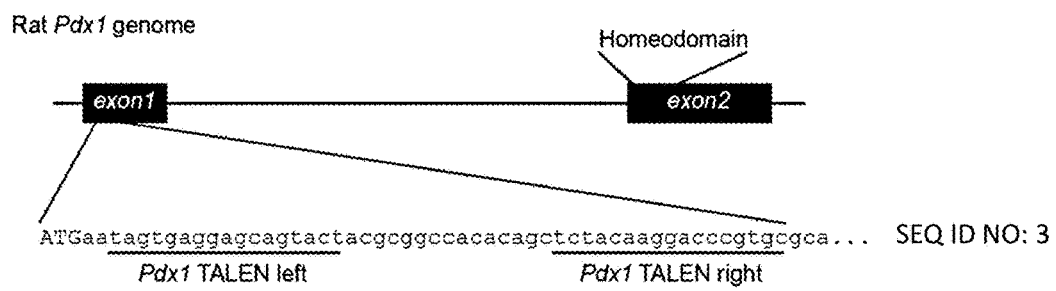

B

```
Wild Type: ATGaatagtgaggagcagtactacgcggccacacagctctacaaggacccgtgcgca...  SEQ ID NO: 3
Mutant A:  ATGaatagtgaggagcagtactacgcggccaca--gctctacaaggacccgtgcgca...  SEQ ID NO: 4
Mutant B:  ATGaatagtgaggagcagtactacgcggc---------tctacaaggacccgtgcgca... SEQ ID NO: 5
Mutant C:  ATGaatagtgaggagcagtactacgc---------gctctacaaggacccgtgcgca...  SEQ ID NO: 6
Mutant D:  ATGaatagtgaggagcagtactacgcgg--------gctctacaaggacccgtgcgca... SEQ ID NO: 7
```

C

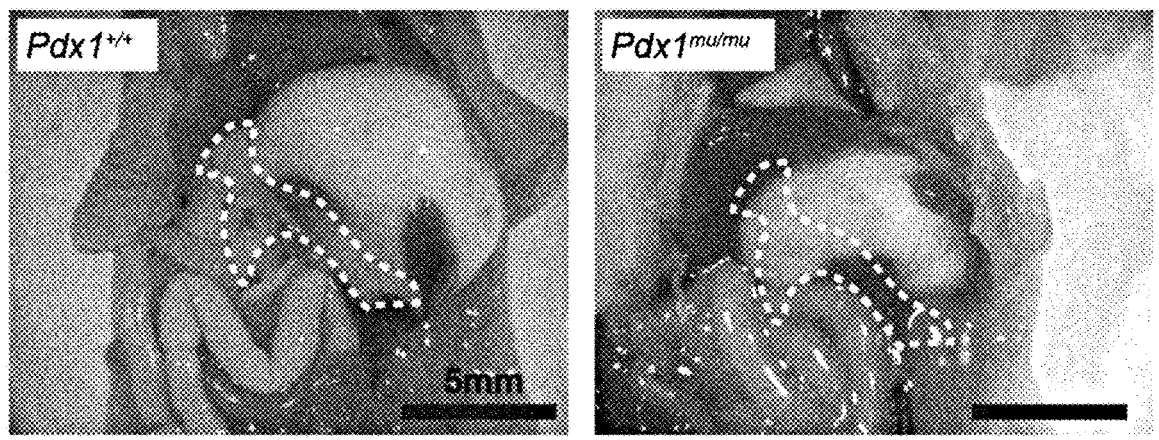

FIG. 2
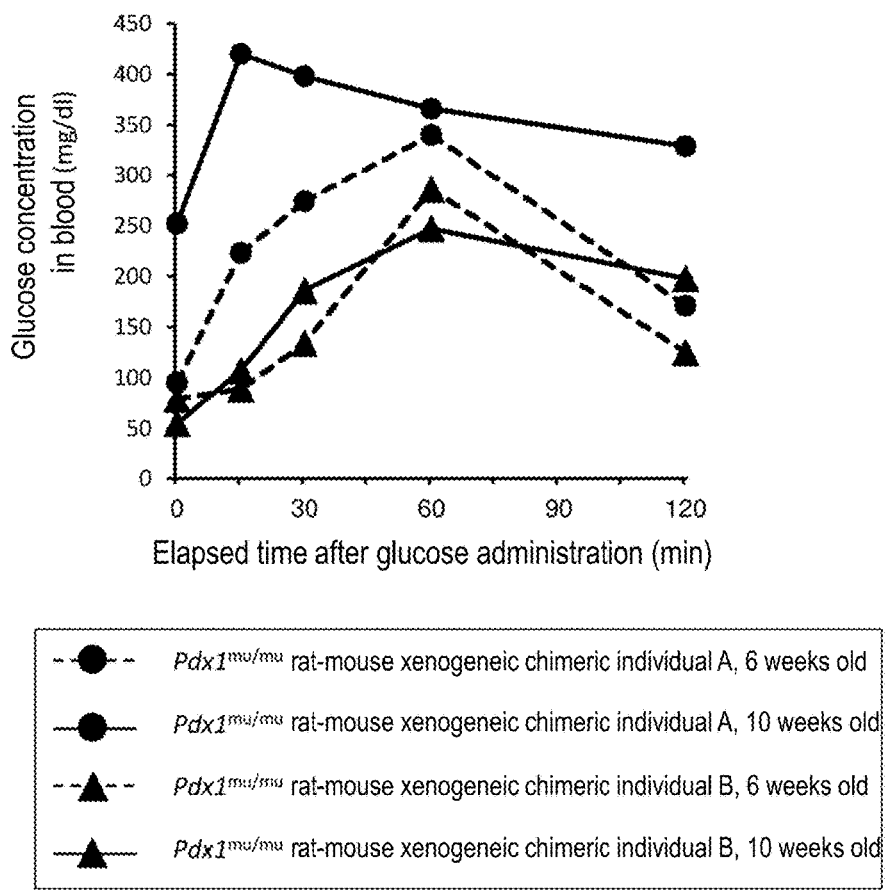
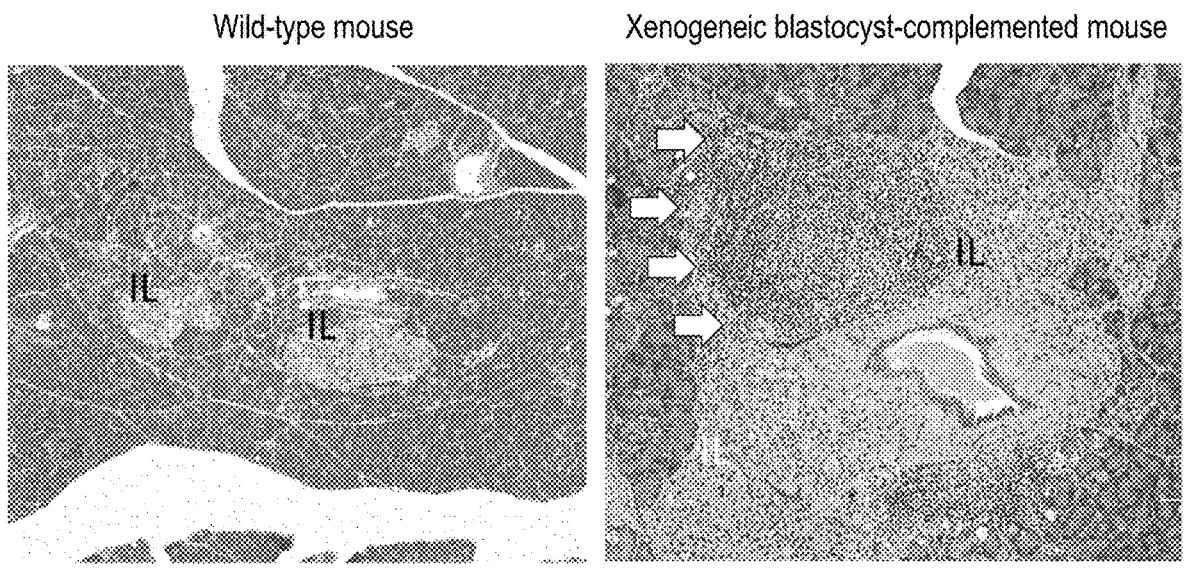

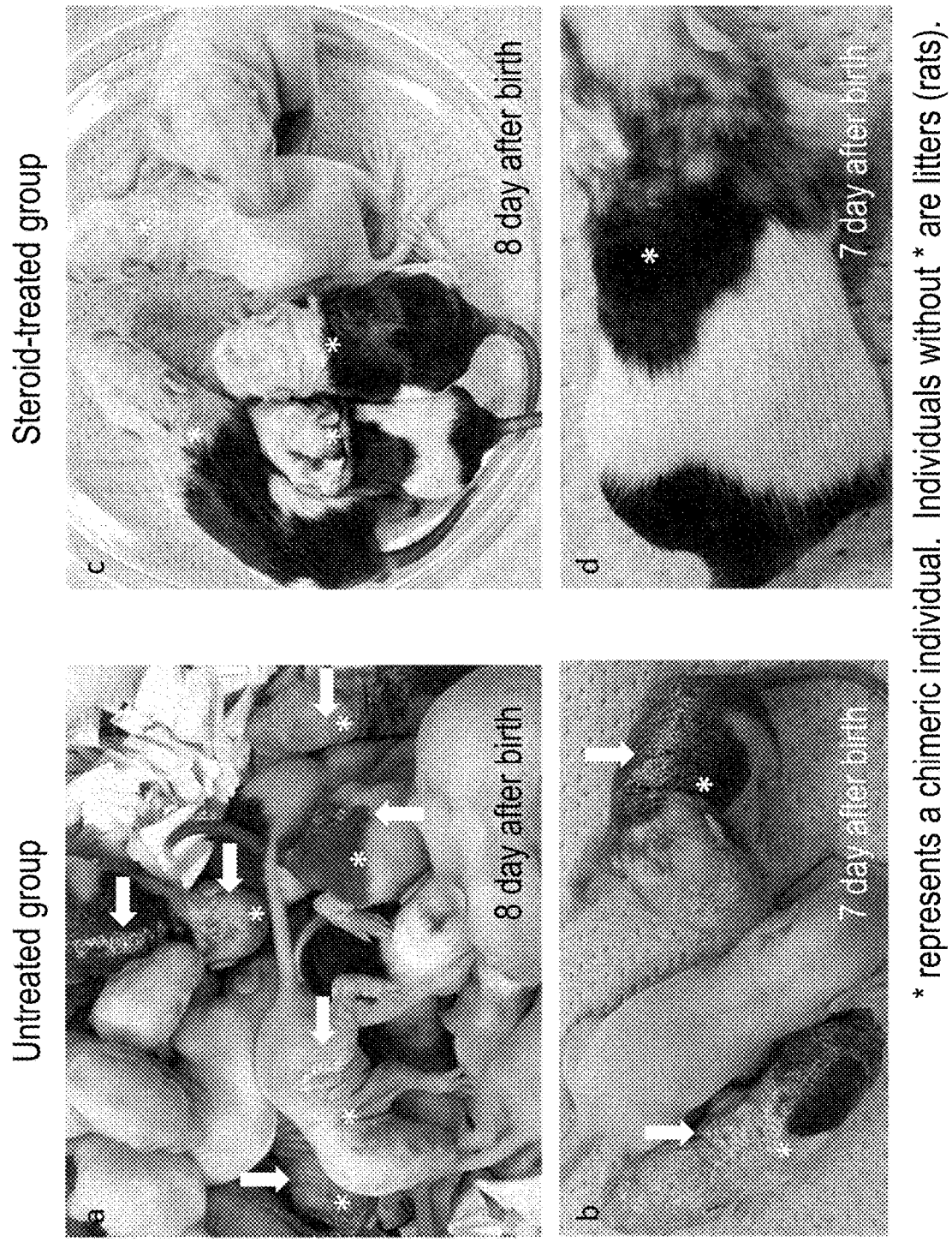

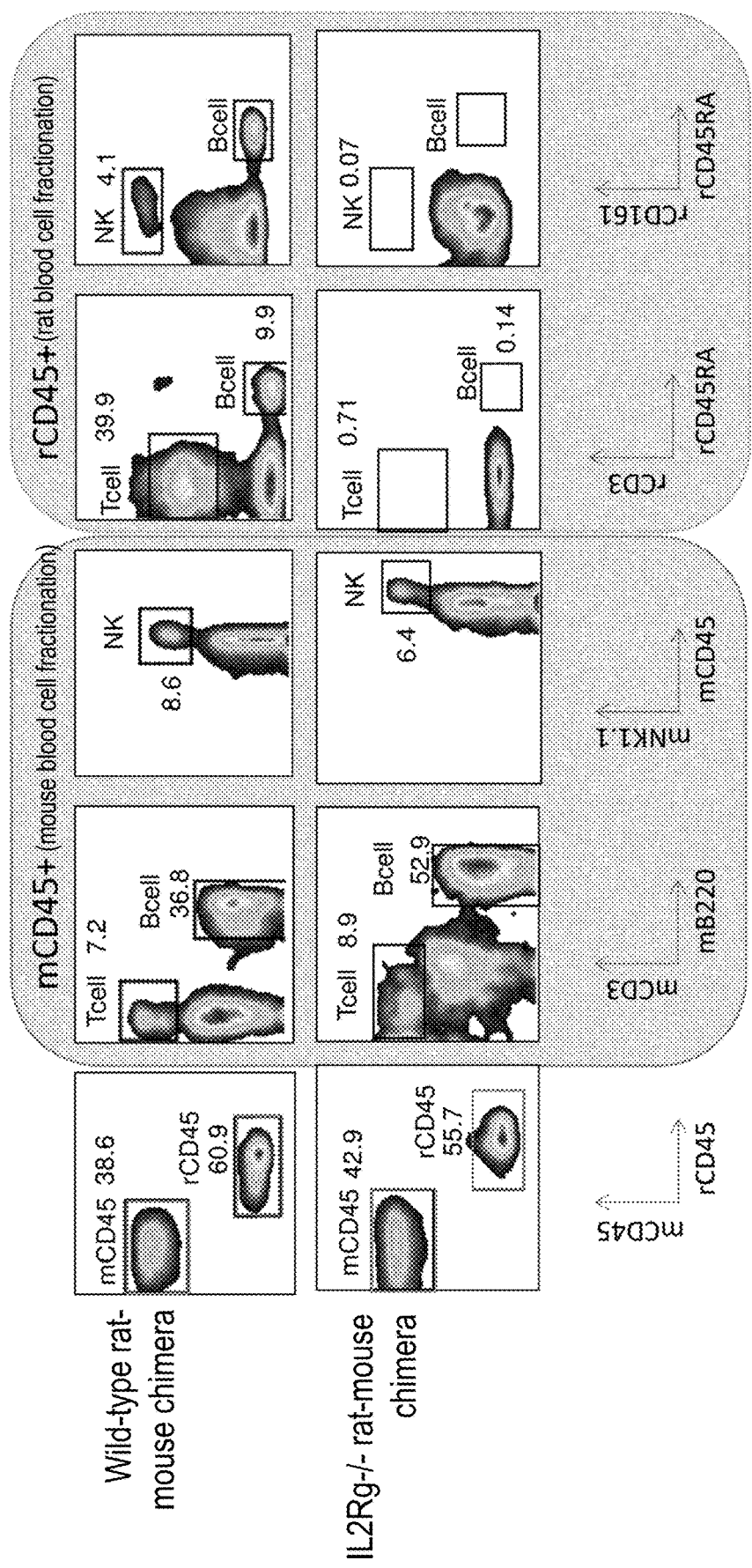

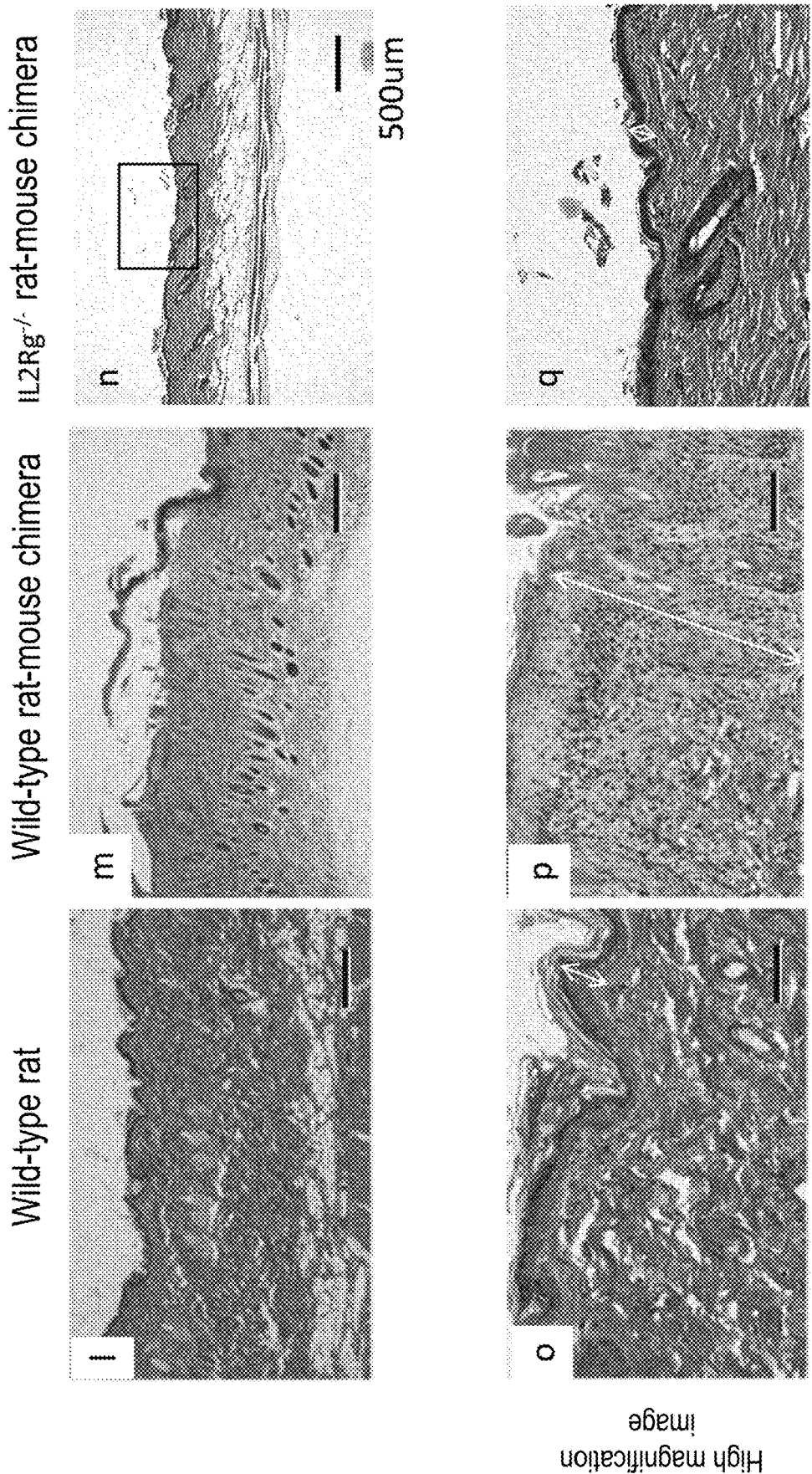

FIG. 8A
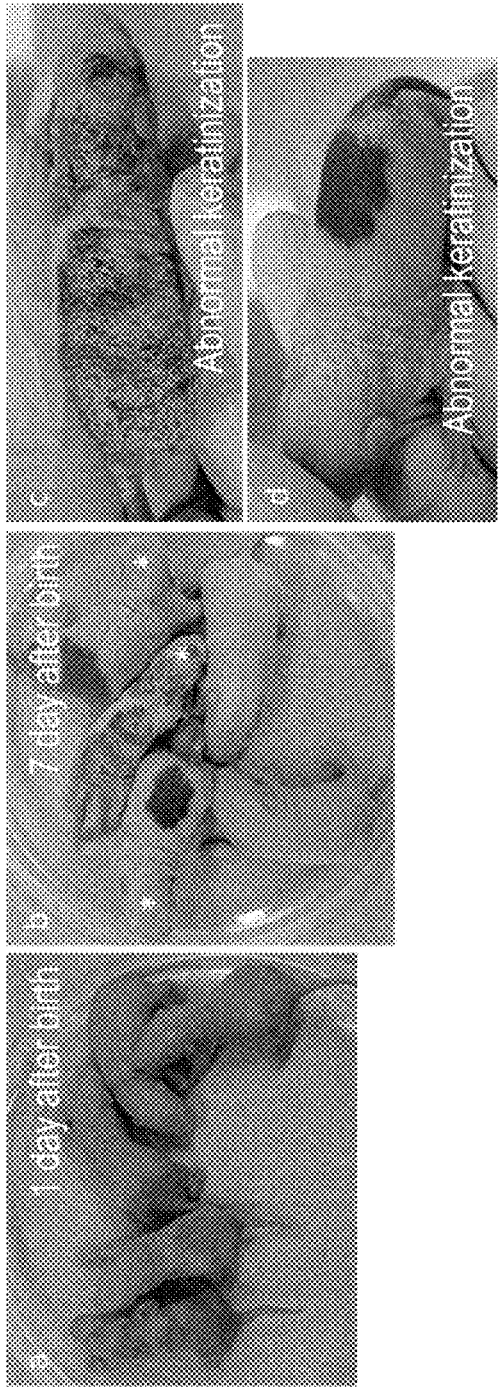
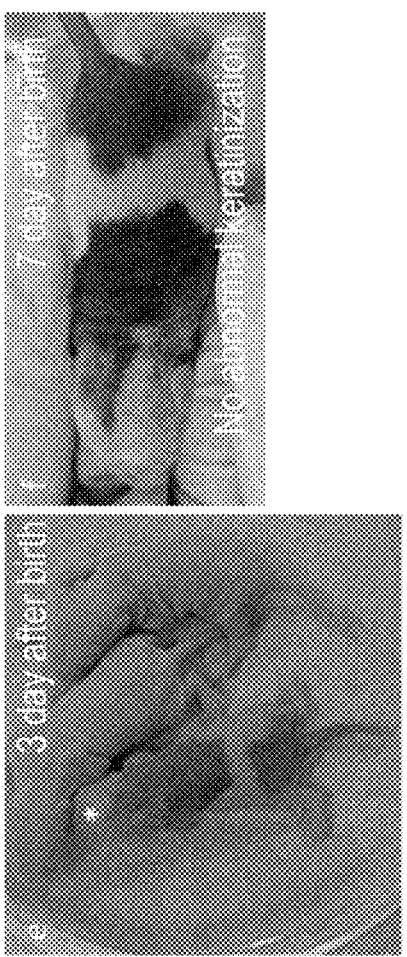

FINDING AND TREATMENT OF INFLAMMATION AFTER BIRTH IN CHIMERIC ANIMAL

TECHNICAL FIELD

The present invention relates to a composition and a method, for use in treating and/or preventing immune response and inflammation that are developed after birth of a chimeric animal, though neither immune response nor inflammation in the fetal period (where the fetus is in a somatic chimeric state) of the animal is manifested.

BACKGROUND ART

In allogeneic chimeric animals prepared by transplanting allogeneic pluripotent stem cells to embryos before implantation, cells derived from the allogeneic pluripotent stem cells coexist with the thymus or lymphocytes before establishment of immunity. Accordingly, the cells derived from the allogeneic pluripotent stem cells are recognized as self and thus are not attacked by the immune system.

In the preparation of xenogeneic chimeric animals as well, xenogeneic cells are recognized as self in principle and thus are not attacked by the immune system, because the xenogeneic cells are introduced to blastocysts before establishment of immunity. Furthermore, neither immune rejection nor inflammatory response has previously been reported as to the xenogeneic chimeric animal, in accordance with the theory described above.

SUMMARY OF INVENTION

Nonetheless, the present inventors have revealed, unexpectedly, born chimeric animals suffer from significant inflammation inside their bodies after birth, though inflammation in the fetal period (where the fetus is in a chimeric state) of these animals has not been reported hitherto. The present invention provides a composition for use in suppressing immune response that is induced after birth, a composition for use in treating and/or preventing inflammation that is developed after birth, a method for suppressing immune response that is induced after birth, and a method for treating and/or preventing inflammation that is developed after birth, for a xenogeneic or allogeneic chimeric animal (e.g., blastocyst-complemented chimeric animal).

The present inventors have found that immune response and inflammation are observed in the epidermis and a donor tissue portion (i.e., a complemented organ or tissue portion in, for example, a blastocyst-complemented chimeric animal) in a born xenogeneic or allogeneic chimeric animal (e.g., blastocyst-complemented chimeric animal). This symptom was rarely observed before birth (in the fetal period). Immune response and inflammatory response in the epidermis were observed in a large number of chimeric animal individuals, and immune response and inflammation in the donor tissue portion were noticeably observed in some individuals. Also, the observed inflammation in the donor tissue portion was associated with the infiltration of leukocytes and the infiltration of macrophages. The immune response and the inflammation were able to be suppressed with a steroid agent. Also, the immune response and the inflammation were able to be suppressed by use of an immunodeficient embryo and/or pluripotent cell. The present invention is based on these findings.

The present invention provides the following aspects:
(1) A composition for use in suppressing immune response or inflammation that occurs in a born xenogeneic or allogeneic chimeric animal (e.g., blastocyst-complemented chimeric animal), the composition comprising an anti-inflammatory agent or an immunosuppressive agent.
(2) The composition according to (1), wherein the immune response or the inflammation is immune response or inflammation that occurs in the skin or immune response or inflammation that occurs in a complemented organ or tissue.
(3) The composition according to (1), wherein the suppression is prophylactically performed.
(4) The composition according to (1) or (2), wherein the anti-inflammatory agent or the immunosuppressive agent comprises steroid.
(5) A method for obtaining an adult from a born xenogeneic or allogeneic chimeric animal (e.g., blastocyst-complemented chimeric animal), the method comprising administering an anti-inflammatory agent or an immunosuppressive agent to the born blastocyst-complemented chimeric animal.
(6) The method according to (5), wherein the anti-inflammatory agent or the immunosuppressive agent is administered before occurrence of immune response or inflammation in the chimeric animal (e.g., blastocyst-complemented chimeric animal).
(7) The method according to (6), comprising:
confirming that the immune response or the inflammation has occurred in the epidermis of the born chimeric animal (e.g., blastocyst-complemented chimeric animal); and
administering the anti-inflammatory agent or the immunosuppressive agent to the chimeric animal (e.g., blastocyst-complemented chimeric animal) thus confirmed to have the immune response or the inflammation.
(8) A method for raising or growing a born xenogeneic or allogeneic chimeric animal (e.g., blastocyst-complemented chimeric animal), the method comprising administering an anti-inflammatory agent or an immunosuppressive agent to the chimeric animal (e.g., blastocyst-complemented chimeric animal), thereby preventing or treating immune response or inflammation in the chimeric animal (e.g., blastocyst-complemented chimeric animal).
(9) A method for obtaining an adult from a born xenogeneic or allogeneic chimeric animal (e.g., blastocyst-complemented chimeric animal), the method comprising administering an anti-inflammatory agent or an immunosuppressive agent to the chimeric animal (e.g., blastocyst-complemented chimeric animal), thereby preventing or treating immune response or inflammation in the chimeric animal (e.g., blastocyst-complemented chimeric animal).
(10) A xenogeneic or allogeneic chimeric animal which is immunodeficient.
(11) An animal having an abnormality that causes failure to form a particular organ or cell, or a pre-implantation embryo thereof which is immunodeficient.
(12) The animal or the pre-implantation embryo thereof according to (11), wherein the organ is an organ selected from the group consisting of the pancreas and the kidney.
(13) The animal according to (11) or (12), wherein the animal having an abnormality that causes failure to form a particular organ or cell is an animal having a genetic modification, selected from: a Pdx1 gene knockout animal, a Pdx1-Hes1 gene transgenic animal, a Sall1 gene knockout animal, a Flk1 gene knockout animal, a Hex gene knockout animal, a Foxa1/Foxa2 gene double knockout animal, an Otx2 gene knockout animal, and a Foxn1 gene knockout animal; an animal having a gene encoding a cell death-inducing factor that is driven by a promoter of any of these genes; and an animal having a gene encoding a cell death-inducing factor that is driven by a promoter of an organ- or cell-specifically expressed gene.

(14) The animal according to any of (11) to (13), wherein the immunodeficiency is associated with a genetic modification or an abnormality in any one or more members selected from IL2Rg, RAG1, RAG2, Foxn1, PRKDC, MHC and SIRPa.

(15) A method for preparing a particular organ or cell in the body of a nonhuman mammal having an abnormality that causes failure to form the organ or the cell, the method comprising
transplanting a mammal pluripotent cell to a pre-implantation embryo of the nonhuman mammal to obtain a chimeric embryo, wherein
any or both of the pluripotent cell and the pre-implantation embryo have a genetic modification or an abnormality resulting in immunodeficiency, and
the pluripotent cell and the pre-implantation embryo are in an allogeneic or xenogeneic relationship.

(16) A composition for use in preparing a chimeric animal, the composition comprising a pluripotent cell having a genetic modification or an abnormality resulting in immunodeficiency.

(17) The composition according to (16), wherein the composition is used to prepare a particular organ or cell in the body of a nonhuman mammal having an abnormality that causes failure to form the organ or the cell.

(18) An organ having a genetic modification or a gene abnormality responsible for immunodeficiency.

BRIEF DESCRIPTION OF DRAWINGS

FIG. 1 shows a TALEN-mediated disruption scheme of a Pdx1 gene region (panel A)(SEQ ID NO: 3), and the gene sequences of this location in disrupted mutants A to D (panel B)(SEQ ID NO: 1—Wild Type; SEQ ID NOs: 4-7, Mutants A-D, respectively). FIG. 1C shows that pdx1$^{mu/mu}$ deletes the pancreas.

FIG. 2 shows results of a glucose tolerance test on 6 weeks after birth and results of a glucose tolerance test on 10 weeks after birth, for rat-mouse blastocyst-complemented chimeric animals (upper diagram of FIG. 2). FIG. 2 also shows that the infiltration of abnormal cells was observed in the pancreatic islet region of a rat-mouse blastocyst-complemented chimeric animal.

FIG. 5 is a diagram showing that dermatitis associated with immune response and inflammation that occurred in rat-mouse chimeric animals was able to be prevented almost completely with an anti-inflammatory agent.

FIG. 7A shows results of blood cell analysis on the peripheral blood of IL2Rg−/− rat-mouse chimeras.

FIG. 7C shows results of histological analysis on the epidermis of IL2Rg−/− rat-mouse chimeras.

FIG. 8A shows abnormal keratinization and thickening in the epidermis of rat-mouse chimeric animals prepared from IL2Rg−/− mouse ES cells and wild-type rat embryos (panels a to d). FIG. 8A also shows the state of the epidermis in rat-mouse chimeric animals prepared from IL2Rg−/− mouse ES cells and IL2Rg−/− rat embryos (panels e and f).

DESCRIPTION OF EMBODIMENTS

Figure 3:
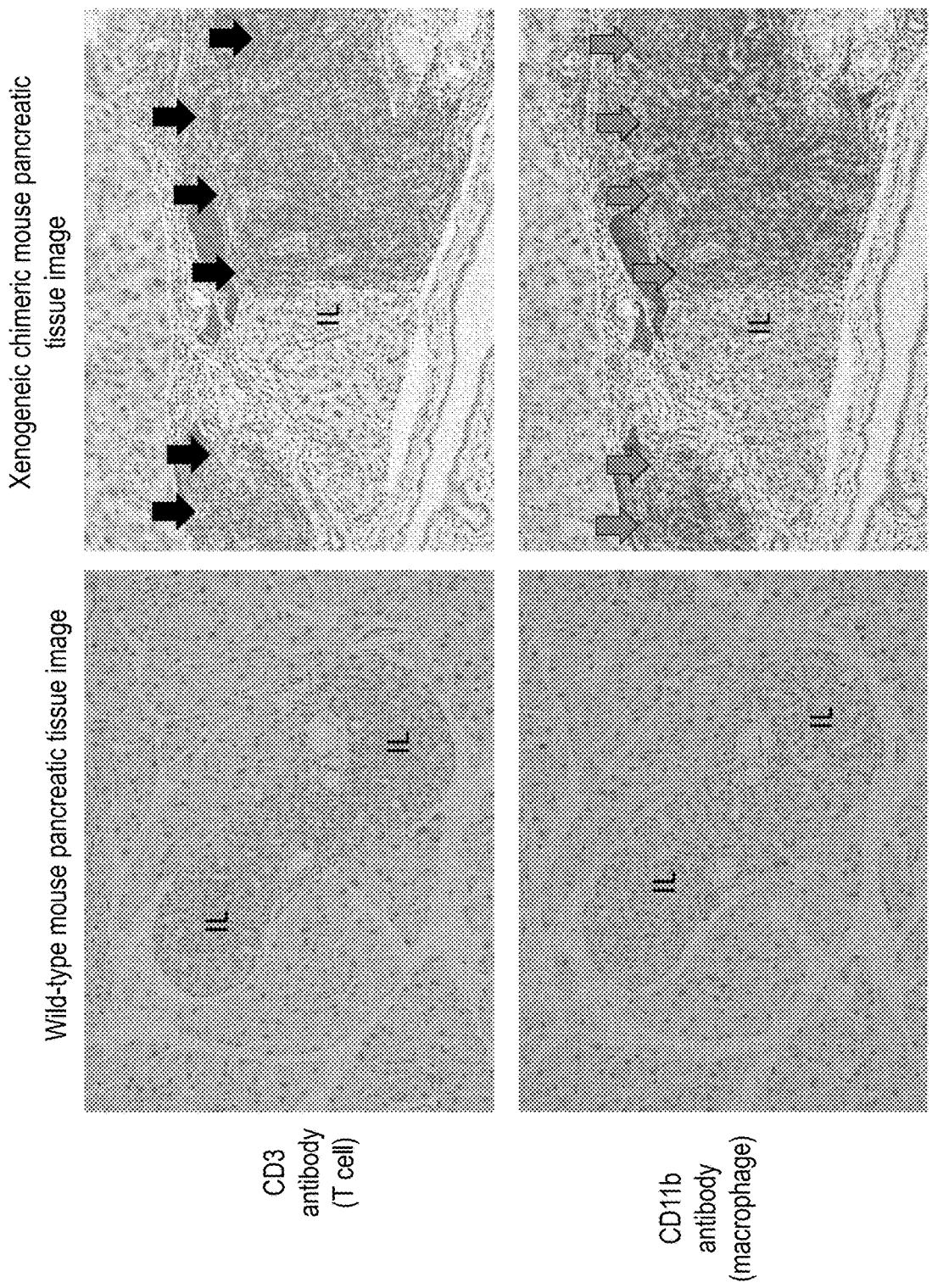
FIG. 3 shows results of conducting immunohistological studies on the location of inflammation in tissues.

In the present specification, the term "chimeric animal" means an individual of a fetus or after birth obtained by growing an embryo obtained by mixing allogeneic or xenogeneic cells (e.g., introducing an allogeneic or xenogeneic pluripotent cell to an embryo such as a pre-implantation embryo) before construction of the immune system. In the present specification, the term "chimeric animal" is used in the meaning including a fetus which is a somatic chimera obtained by introducing an allogeneic or xenogeneic cell to an embryo, and an individual after birth obtained from the fetus. Such a chimeric animal is considered to be in a state immunotolerant to the introduced cell. In the present specification, the term "blastocyst-complemented chimeric animal" means an individual of a fetus or after birth obtained by introducing an allogeneic or xenogeneic cell to a blastocyst and growing the obtained blastocyst. The chimeric animal (e.g., blastocyst-complemented chimeric animal) may be established between a mammal blastocyst and a mammal cell. The blastocyst-complemented chimeric animal may be established between a mammal blastocyst and a mammal pluripotent cell. In the blastocyst-complemented chimeric animal, a defect (e.g., the deletion of an organ or a tissue, particularly, a cell-autonomous defect or cell-autonomous deletion of an organ or a tissue) possessed by the blastocyst is compensated for by an externally introduced allogeneic or xenogeneic cell, thereby alleviating, reducing, or completely eliminating the original defect. One useful example of the blastocyst-complemented chimeric animal includes a recipient animal in which a particular organ or cell cannot be formed and is instead taken over by a donor cell to complement the deleted organ or tissue. Examples of the abnormality that causes failure to form a particular organ or cell include an abnormality that causes cell-autonomous failure to form an organ or a cell. In the present specification, the term "cell-autonomous" means an abnormality possessed by a cell substantially has qualitative or quantitative influence only on the cell.

In the present specification, the term "immunotolerance" means a state where immune response specific for a particular antigen has been lost or a state where the immune response has been suppressed. The immune system does not respond to a self-antigen presented by self-MHC. Such a phenomenon is called "self-tolerance". In the body, cells strongly reactive with a self-antigen are killed in the process of T cell maturation in the thymus so as not to produce immunocytes attacking the self-antigen in response to this self-antigen. Thus, it is considered that foreign cells introduced before establishment of the immune system (e.g., at the blastocyst stage) are recognized as self in an individual and thus the immune system does not respond to the cells (self-tolerance has been established).

In the present specification, the term "mammal" includes: primates such as humans and monkeys; livestock animals such as pigs, goats, sheep, and horses; and pet animals such as dogs and cats. However, in the present specification, the recipient animal is nonhuman, unless otherwise specified.

In the present specification, the term "pluripotent cell" means a cell having pluripotency. Examples of the pluripotent cell include inner cell masses, and pluripotent stem cells such as embryonic stem cells (ES cells) and induced pluripotent stem cells (iPS cells).

In the present specification, the term "xenogeneic" means that a recipient and a donor are of different species. The term "xenogeneic" may mean between the same genera, between the same families, between the same orders, or between the same classes. In the present specification, the term "allogeneic" means that a recipient and a donor are different individuals of the same species.

In the present specification, the term "donor" means a cell to be introduced to a pre-implantation embryo such as a blastocyst, or an animal from which the cell is derived. In the present specification, the term "recipient" means a pre-implantation embryo such as a blastocyst, or an animal from which the pre-implantation embryo such as a blastocyst is derived.

In the present specification, the term "inflammation" refers to pathological change that is caused as a result of the response of cells of the immune system. In the present specification, the inflammation particularly refers to inflammation that is noticeably observed around donor cells after birth in a xenogeneic or allogeneic chimeric animal. Inflammation induced by immune response between a donor and a recipient is not significantly observed before birth and is observed after birth.

In the present specification, the term "immune response" refers to response that occurs against non-self through the recognition of the non-self. In the present specification, the immune response particularly refers to immune response that is noticeably observed near donor cells after birth in a xenogeneic or allogeneic chimeric animal. Immune response between a donor and a recipient is not significantly observed before birth and is observed after birth.

In the present specification, the term "anti-inflammatory agent" means a drug for use in suppressing inflammation. In the present specification, the term "immunosuppressive agent" means a drug for use in suppressing immune functions. In the present specification, the term "anti-inflammatory agent or immunosuppressive agent" means "anti-inflammatory agent and immunosuppressive agent", "anti-inflammatory agent" or "immunosuppressive agent". Examples of the immunosuppressive agent include drugs for use in suppressing innate immunity, and drugs for use in suppressing acquired immunity. Some drugs, such as a steroid agent, possess both an anti-inflammatory effect and an anti-immune effect.

The present inventors have found that immune response and inflammation are observed in the epidermis and a donor tissue portion (i.e., a complemented organ or tissue portion in, for example, a blastocyst-complemented chimeric animal) in a born xenogeneic or allogeneic chimeric animal (e.g., blastocyst-complemented chimeric animal). This immune response or inflammation was rarely observed before birth (in the fetal period) of the xenogeneic or allogeneic chimeric animal. Immune response or inflammation in the epidermis was observed in a large number of chimeric animal individuals, whereas immune response or inflammation in the donor tissue portion was observed only in some individuals. Also, the observed immune response or inflammation in the donor tissue portion was associated with the infiltration of leukocytes and the infiltration of macrophages. The immune response and the inflammation were able to be suppressed with a steroid agent.

Thus, the present invention provides a composition for use in suppressing immune response or inflammation that occurs in a born xenogeneic or allogeneic chimeric animal (e.g., blastocyst-complemented chimeric animal), the composition comprising an anti-inflammatory agent or an immunosuppressive agent. The composition of the present invention can be administered, for example, before birth, during birth, after birth, and/or after development of inflammation.

In the present invention, immune response or inflammation can be prevented by administering the anti-inflammatory agent or the immunosuppressive agent to the xenogeneic or allogeneic chimeric animal (e.g., blastocyst-complemented chimeric animal), for example, immediately after birth (e.g., within several days after birth), because the immune response or the inflammation occurs after birth. In the present invention, immune response or inflammation may be prevented by administering the anti-inflammatory agent or the immunosuppressive agent to the xenogeneic or allogeneic chimeric animal (e.g., blastocyst-complemented chimeric animal) from before birth. In this way, according to the present invention, the immune response or the inflammation that occurs in a born xenogeneic or allogeneic chimeric animal (e.g., blastocyst-complemented chimeric animal) can be prevented. In an embodiment of the present invention, neither the anti-inflammatory agent nor the immunosuppressive agent can be administered before birth. In this context, in the present specification, the term "prevention" means that the procedure is performed before occurrence of immune response or inflammation, thereby reducing the severity of immune response or inflammation, or eliminating the occurrence of immune response or inflammation (decreasing the incidence thereof), as compared with the absence of the procedure.

In the present invention, immune response or inflammation was not clearly observed in all individuals. Thus, in the present invention, the suppression of immune response or inflammation is used in the meaning including decrease in the incidence of immune response or inflammation. Specifically, the present invention provides a composition for use in decreasing the incidence of immune response or inflammation that occurs in a born xenogeneic or allogeneic chimeric animal (e.g., blastocyst-complemented chimeric animal), the composition comprising an anti-inflammatory agent or an immunosuppressive agent.

In the present invention, immune response or inflammation may be treated by administering the anti-inflammatory agent or the immunosuppressive agent to the xenogeneic or allogeneic chimeric animal (e.g., blastocyst-complemented chimeric animal) after observation of the immune response or the inflammation after birth. In this aspect, for example, the immunosuppressive agent does not have to be administered if no immune response is observed, and the anti-inflammatory agent does not have to be administered if no inflammation is observed. In this context, in the present specification, the term "treatment" means that the procedure is performed after occurrence of immune response or inflammation, thereby reducing the severity of immune response or inflammation, or eliminating the occurrence of immune response or inflammation, as compared with the absence of the procedure.

In an aspect, the present invention provides a composition for use in preventing and/or treating immune response or inflammation that occurs after birth in a born xenogeneic or allogeneic chimeric animal (e.g., blastocyst-complemented chimeric animal), the composition comprising an anti-inflammatory agent or an immunosuppressive agent.

In an aspect, the present invention provides a method for preventing and/or treating immune response or inflammation that occurs after birth in a born xenogeneic or allogeneic chimeric animal (e.g., blastocyst-complemented chimeric animal), the method comprising administering an anti-inflammatory agent or an immunosuppressive agent to the animal.

In an aspect, the present invention provides a method for raising a born xenogeneic or allogeneic chimeric animal (e.g., blastocyst-complemented chimeric animal), the method comprising administering an anti-inflammatory agent or an immunosuppressive agent to the animal. Immune response or inflammation that occurs in the epidermis or an organ or a tissue of the born xenogeneic or allogeneic chimeric animal (e.g., blastocyst-complemented chimeric animal) can be prevented and/or treated by administering the anti-inflammatory agent or the immunosuppressive agent to the animal during raising.

In an aspect, the present invention provides feed for a born xenogeneic or allogeneic chimeric animal (e.g., blastocyst-complemented chimeric animal), the feed comprising an anti-inflammatory agent or an immunosuppressive agent.

In an aspect, the present invention provides a method for raising or growing a born xenogeneic or allogeneic chimeric animal (e.g., blastocyst-complemented chimeric animal), the method comprising administering an anti-inflammatory agent or an immunosuppressive agent to the chimeric animal (e.g., blastocyst-complemented chimeric animal), thereby preventing and/or treating immune response or inflammation in the chimeric animal (e.g., blastocyst-complemented chimeric animal), or decreasing the incidence of immune response or inflammation.

In an aspect, the present invention provides a method for obtaining an adult from a born xenogeneic or allogeneic chimeric animal (e.g., blastocyst-complemented chimeric animal), the method comprising administering an anti-inflammatory agent or an immunosuppressive agent to the chimeric animal (e.g., blastocyst-complemented chimeric animal), thereby preventing and/or treating immune response or inflammation in the chimeric animal (e.g., blastocyst-complemented chimeric animal), or decreasing the incidence of immune response or inflammation.

The anti-inflammatory agent or the immunosuppressive agent may comprise an excipient in addition to an active ingredient. The anti-inflammatory agent or the immunosuppressive agent can be administered for immune response or inflammation in the epidermis, for example, by topical application to the location of the immune response or the inflammation in the epidermis. The anti-inflammatory agent or the immunosuppressive agent can be properly administered by oral administration or parenteral administration (e.g., intravenous, intramuscular, intra-inflammatory tissue, or intraperitoneal administration). The anti-inflammatory agent or the immunosuppressive agent may be systemically administered or may be topically administered to an affected part. Those skilled in the art can easily determine the dose of the anti-inflammatory agent or the immunosuppressive agent as an amount necessary for suppressing immune response or inflammation.

Examples of the immunosuppressive agent include, but are not particularly limited to: cyclosporin and tacrolimus as calcineurin inhibitors; rapamycin and everolimus as mTOR inhibitors; azathioprine, mizoribine, methotrexate, mycophenolate mofetil, and leflunomide as antimetabolites; and cyclophosphamide as an alkylating agents, any of which can be used in the present invention.

Examples of the anti-inflammatory agent include, but are not particularly limited to, steroidal anti-inflammatory drugs (SAIDs) and non-steroidal anti-inflammatory drugs (NSAIDs), any of which can be used in the present invention. Examples of the steroid include cortisol, prednisolone, triamcinolone, beclomethasone, betamethasone, fluticasone, dexamethasone, and hydrocortisone, any of which can be used in the present invention. Other examples of the anti-inflammatory agent include inflammatory cytokine inhibitors such as anti-inflammatory cytokine antibodies, for example, anti-TNF-α antibodies, and antibodies against soluble cytokines, for example, soluble TNF receptors, any of which can be used in the present invention.

In an embodiment of the present invention, a steroidal anti-inflammatory agent having a function as the immunosuppressive agent and a function as the anti-inflammatory agent may be preferably used. In an embodiment of the present invention, a combination of the immunosuppressive agent and the anti-inflammatory agent may be administered in order to suppress immune response and inflammatory response that occur after birth in a xenogeneic or allogeneic chimeric animal (e.g., blastocyst-complemented chimeric animal). However, in the present invention, even the mere suppression of either immune response or inflammation can be expected to produce a sufficient effect.

In an aspect, the present invention provides a composition for use in improving the probability of production of a functional organ or tissue in a born xenogeneic or allogeneic chimeric animal (e.g., blastocyst-complemented chimeric animal), the composition comprising an anti-inflammatory agent or an immunosuppressive agent. In an aspect, the present invention provides a method for improving the probability of production of a functional organ or tissue in the xenogeneic or allogeneic chimeric animal (e.g., blastocyst-complemented chimeric animal) of the present invention, the method comprising administering an anti-inflammatory agent or an immunosuppressive agent to the born xenogeneic or allogeneic chimeric animal (e.g., blastocyst-complemented chimeric animal). The anti-inflammatory agent or the immunosuppressive agent or the composition comprising the anti-inflammatory agent or the immunosuppressive agent can be administered to the xenogeneic or allogeneic chimeric animal (e.g., blastocyst-complemented chimeric animal) after birth, thereby suppressing immune response or inflammation that has occurred in the body or the epidermis.

In an aspect, the present invention provides a method for producing a functional organ or tissue in a born xenogeneic or allogeneic blastocyst-complemented chimeric animal, the method comprising administering an anti-inflammatory agent or an immunosuppressive agent to the born xenogeneic or allogeneic blastocyst-complemented chimeric animal. Many individuals of born xenogeneic or allogeneic blastocyst-complemented chimeric animals suffer from some immune response or inflammation (only some individuals suffer from noticeable immune response or inflammation). Thus, the occurrence of immune response or inflammation is suppressed by administering the anti-inflammatory agent or the immunosuppressive agent to the born xenogeneic or allogeneic blastocyst-complemented chimeric animal. The function of the resulting organ or tissue is enhanced as compared with the case of not administering the anti-inflammatory agent or the immunosuppressive agent. In an embodiment, the present invention provides a method for producing plurality of functional organs or tissues in a plurality of born xenogeneic or allogeneic blastocyst-complemented chimeric animals, the method comprising administering an anti-inflammatory agent or an immunosuppressive agent to each of the plurality of born xenogeneic or allogeneic blastocyst-complemented chimeric animals. In the case of producing functional organs or tissues in a plurality of, 5 or more, 10 or more, 20 or more, 30 or more, 40 or more, or 50 or more born xenogeneic or allogeneic blastocyst-complemented chimeric animals by this method, a larger number of functional organs or tissues can be obtained as compared with the case of not administering the anti-inflammatory agent or the immunosuppressive agent.

Since it is considered that acquired immune tolerance has been established in the xenogeneic or allogeneic chimeric animal (e.g., blastocyst-complemented chimeric animal) of the present invention, the composition of the present invention may not comprise an immunosuppressive agent of acquired immunity. Thus, in an embodiment of the present invention, the composition or the anti-inflammatory agent or the immunosuppressive agent of the present invention comprises no immunosuppressive agent of acquired immunity. However, in another embodiment of the present invention, the composition of the present invention may comprise an immunosuppressive agent of acquired immunity.

The present invention provides an organ consisting substantially of a donor cell, the organ having the function and form of the organ of a recipient.

The present invention provides a method for producing an organ consisting substantially of a donor cell in the body of a xenogeneic blastocyst-complemented chimeric animal, the method comprising: introducing a donor pluripotent cell to a blastocyst of a recipient animal having an abnormality that causes failure to form a particular organ or cell; transplanting the blastocyst to the uterus of a pseudopregnant female host; giving birth to a blastocyst-complemented chimeric animal; and treating the born animal with an anti-inflammatory agent or an immunosuppressive agent.

The present invention provides an organ consisting substantially of a donor cell, the organ having the function and form of the organ of a recipient, wherein the form of the organ of the recipient is different from that of the donor.

The present invention provides a method for producing an organ consisting substantially of a donor cell in the body of a xenogeneic blastocyst-complemented chimeric animal, the method comprising: introducing a donor pluripotent cell to a blastocyst of a recipient animal having an abnormality that causes failure to form a particular organ or cell; transplanting the blastocyst to the uterus of a pseudopregnant female host; giving birth to a blastocyst-complemented chimeric animal; and treating the born animal with an anti-inflammatory agent or an immunosuppressive agent, wherein the form of the organ of the recipient is different from that of the donor.

In the present specification, the phrase "the form of the organ of the recipient is different from that of the donor" means that the organ forms (size and/or shape) differ from each other morphologically taxonomically.

The xenogeneic or allogeneic chimeric animal (e.g., blastocyst-complemented chimera) can be obtained, for example, as follows: first, a nonhuman mammal pre-implantation embryo (e.g., blastocyst) is obtained. Next, a pluripotent cell that is xenogeneic or allogeneic with respect to the pre-implantation embryo (e.g., blastocyst) is obtained. For example, an inner cell mass, an ES cell or an iPS cells can be used as the pluripotent cell. Those skilled in the art can appropriately prepare these cells. The xenogeneic or allogeneic pluripotent cell is introduced to the obtained pre-implantation embryo (e.g., blastocyst). For example, the xenogeneic or allogeneic pluripotent cell can be introduced to the cavity of the pre-implantation embryo (e.g., blastocyst). The resultant is transplanted to the uterus of a pseudopregnant female host and grown to obtain a fetus. Further, after delivery, a born xenogeneic or allogeneic chimera (e.g., blastocyst-complemented chimera) is obtained. A chimera (e.g., blastocyst complementation) is established without any problem even between species differing in size by 10 or more times. Thus, for example, a xenogeneic chimera (e.g., blastocyst-complemented chimera) can be accomplished between mammals differing in average body size by 10 or less times. Also, a chimera (e.g., blastocyst-complemented chimera) is established without any problem between different species having 80% or higher (e.g., 90% or higher or 95% higher) identity as to the coding sequences of genes. Thus, chimeric formation can be established or blastocyst complementation can be accomplished between mammals having 80% or higher identity as to the coding sequences of genes. In an embodiment of the present invention, chimeric formation or blastocyst complementation is accomplished between mammals differing in average body size by 10 or less times and having 80% or higher (e.g., 90% or higher or 95% or higher) identity as to the coding sequences of genes. A human and a pig or a human and sheep differ in average body size by 10 or less times and have 80% or higher (e.g., 90% or higher or 95% or higher) identity as to the coding sequences of genes, and a combination thereof has past results of tissue transplantation such as skin transplantation and is preferred in the present invention.

The present invention provides a xenogeneic or allogeneic chimeric animal which is immunodeficient. In an embodiment of the present invention, the chimeric animal may have a genetic modification. In an embodiment of the present invention, the chimeric animal may have an abnormality that causes failure to form a particular organ or cell. In an embodiment of the present invention, the chimeric animal may be prepared from a pluripotent cell containing a genetic modification or an abnormality resulting in immunodeficiency, and a non-immunodeficient pre-implantation embryo. In an embodiment of the present invention, the chimeric animal may be prepared from a pre-implantation embryo containing a genetic modification or an abnormality resulting in immunodeficiency, and a non-immunodeficient pluripotent cell. In an embodiment, the chimeric animal may be prepared from a pluripotent cell and a pre-implantation embryo each independently containing a genetic modification or an abnormality resulting in immunodeficiency.

In the present specification, the term "immunodeficiency" is used in the meaning including a state where immune response is wholly or partially suppressed. The immunodeficiency also includes a decreased function of the innate immune system, for example, partial or whole suppression of complement pathway activation, avoidance of macrophage or monocyte phagocytosis, and inhibition of cytotoxicity by NK cells. In an embodiment of the present invention, one or more members selected from the group consisting of IL2Rg, RAG1, RAG2, Foxn1, PRKDC, MHC and SIRPa are deleted, or modified or disrupted in the immunodeficiency. In an embodiment of the present invention, genes of one or more members selected from the group consisting of IL2Rg, RAG1, RAG2, Foxn1, and PRKDC are deleted, or modified or disrupted in the immunodeficiency. In an embodiment of the present invention, genes of one or more members selected from the group consisting of IL2Rg and RAG2 are deleted, or modified or disrupted in the immunodeficiency. In an embodiment of the present invention, the immunodeficiency is attributed to a modification of a gene essential for the development and maintenance of the immune system, or a modification of a gene that weakens immune response. The immunodeficiency may be, for example, immunodeficiency ascribable to insufficient functions of one or more genes selected from the group consisting of IL2Rg gene, RAG1 gene, RAG2 gene, Foxn1 gene, PRKDC gene, Hc (C5) gene, MHC gene (gene encoding class I and/or gene encoding class II) and SIRPa gene.

The present invention provides an animal having an abnormality that causes failure to form a particular organ or cell, or a pre-implantation embryo thereof which is immunodeficient. The pre-implantation embryo of such an animal may be grown into a chimeric animal (e.g., allogeneic chimeric animal and xenogeneic chimeric animal) having an organ derived from a transplanted pluripotent cell by transplanting a pluripotent cell (e.g., wild-type pluripotent cell) having the ability to form the organ. In this respect, an immunodeficient pluripotent cell may be used as the pluripotent cell to be transplanted, and inflammation in the resulting chimeric animal can be further alleviated. In an embodiment, the animal is a nonhuman mammal. In an embodiment, the nonhuman mammal may contain human cells in the body.

The present invention provides
a method for preparing a particular organ or cell in the body of a nonhuman mammal having an abnormality that causes failure to form the organ or the cell, the method comprising
transplanting a mammal pluripotent cell to a pre-implantation embryo of the nonhuman mammal to obtain a chimeric embryo, wherein
any or both of the pluripotent cell and the pre-implantation embryo have a genetic modification or an abnormality resulting in immunodeficiency, and
the pluripotent cell and the pre-implantation embryo are in an allogeneic or xenogeneic relationship. When the pluripotent cell has a genetic modification or an abnormality resulting in immunodeficiency, the resulting organ has a genetic modification or an abnormality responsible for immunodeficiency.

In an embodiment of the present invention, the method for preparing a particular organ in the body of a nonhuman mammal having an abnormality that causes failure to form the organ or the cell may further comprise transplanting the chimeric embryo to the uterus of a female host (e.g., pseudopregnant female host). In an embodiment of the present invention, the method for preparing a particular organ or cell in the body of a nonhuman mammal having an abnormality that causes failure to form the organ or the cell may further comprise obtaining a newborn from the chimeric embryo. In an embodiment of the present invention, the method for preparing a particular organ or cell in the body of a nonhuman mammal having an abnormality that causes failure to form the organ or the cell may further comprise growing the newborn obtained from the chimeric embryo. In an embodiment of the present invention, the method for preparing a particular organ or cell in the body of a nonhuman mammal having an abnormality that causes failure to form the organ or the cell may further comprise growing the newborn into an adult. In an embodiment of the present invention, the method for preparing a particular organ or cell in the body of a nonhuman mammal having an abnormality that causes failure to form the organ or the cell may further comprise administering one or more agents selected from the group consisting of an immunosuppressive agent and an anti-inflammatory agent to the nonhuman mammal thus obtained.

In an embodiment of the present invention, examples of the nonhuman mammal having an abnormality that causes failure to form a particular organ or cell include, but are not particularly limited to, nonhuman mammals having a gene encoding a cell death-inducing factor that is driven by a promoter of an organ- or cell-specifically expressed gene. The gene encoding a cell death-inducing factor can be driven, as described above, by the promoter of an organ- or cell-specifically expressed gene so that cell death is induced in the particular organ or the particular cell. As a result, the nonhuman mammal cannot produce the organ or the cell. On the other hand, a cell (e.g., pluripotent cell) that can contribute to the organ or the cell can be introduced to such a nonhuman mammal so that the organ or the cell supposed to be lost in the nonhuman mammal is complemented by the introduced cell. As a result, the organ or the cell consisting of the introduced cell can be prepared in the body of the nonhuman mammal. Examples of the cell death-inducing factor include cytotoxic genes such as caspase-8, caspase-9, Barnase, and diphtheria toxin, any of which can be used in the present invention. Examples of the promoter of an organ- or cell-specifically expressed gene include Alb promoter and CD45 promoter, any of which can be used in the present invention.

In an embodiment of the present invention, the nonhuman mammal having an abnormality that causes failure to form a particular organ or cell is not particularly limited, and, for example, a gene knockout nonhuman mammal or a transgenic nonhuman mammal having the abnormality that causes failure to form a particular organ or cell can be used. Examples of such a transgenic animal or a knockout animal include Pdx1 gene knockout animals, Pdx1-Hes1 gene transgenic animals, Sall1 gene knockout animals, Flk1 gene knockout animals, Hex gene knockout animals, Foxa1/Foxa2 gene double knockout animals, Otx2 gene knockout animals, and Foxn1 gene knockout animals, any of which can be used in the present invention. It is known that the pancreas is deleted in, for example, a Pdx1 gene knockout animal or a Pdx1-Hes1 gene transgenic animal. It is known that the kidney is deleted in a Sall1 gene knockout animal. It is known that these organs are each complemented by an organ consisting of a pluripotent cell-derived cell by introducing a pluripotent cell to an embryo having the genetic modification described above. In an embodiment of the present invention, the nonhuman mammal having an abnormality that causes failure to form a particular organ or cell is not particularly limited, and, for example, a nonhuman mammal cell-autonomously having the abnormality that causes failure to form a particular organ or cell can be used. In the present invention, the "abnormality that causes failure to form a cell" is used in the meaning including an abnormality that causes failure to form a hematopoietic cell, a blood cell or a hematopoietic system.

The present invention provides a composition for use in preparing a chimeric animal, the composition comprising a pluripotent cell having a genetic modification or an abnormality resulting in immunodeficiency. The present invention provides a composition for use in preparing a particular organ or cell in the body of a nonhuman mammal having an abnormality that causes failure to form the organ or the cell, the composition comprising a pluripotent cell having a genetic modification or an abnormality resulting in immunodeficiency.

In these embodiments, the pluripotent cell is a pluripotent cell having the ability to form a chimera. In an embodiment, the pluripotent cell may be a mammal (e.g., human) pluripotent cell such as an ES cell or an iPS cell. In an embodiment, the method for preparing the chimeric animal is as mentioned above. In an embodiment, the pluripotent cell may have an additional genetic modification or abnormality in addition to the genetic modification or the abnormality resulting in immunodeficiency. In an embodiment, the pluripotent cell may not have an additional genetic modification or abnormality in addition to the genetic modification or the abnormality resulting in immunodeficiency. In an embodiment, the pluripotent cell may be a human ES cell or a human iPS cell. In an embodiment, the pluripotent cell may be a human inner cell mass (human ICM). In an embodiment, the pluripotent cell may be a cell that has undergone apoptosis suppression treatment. In an embodiment, the pluripotent cell may be a cell overexpressing an apoptosis suppressor gene. In an embodiment, the pluripotent cell may have the ability to form a colony in a state dispersed as single cells.

EXAMPLES

Example 1: Preparation of Xenogeneic Chimeric Animal

In this Example, the pancreas consisting of mouse cells was prepared in rats obtained by introducing mouse pluripotent stem cells to blastocysts of apancreatic rats and growing the blastocysts.

(1) Preparation of Apancreatic Rat

Apancreatic rats were prepared by introducing a mutation into a Pdx1 coding region in the same way as that performed for mice (Takahashi, R., et al., Transgenic Res. 8, 397-400 (1999)). The rats used were Wister rats (purchased from Japan SLC, Inc.). Specifically, as shown in FIG. 1A, in vitro transcribed mRNAs of Pdx1 TAL effector nucleases (TALENs) targeting regions 3 bp downstream and 35 bp downstream, respectively, from Pdx1 start codon (3 ng/µl or 10 ng/µl each of the mRNAs) were injected to the nuclei of male rat zygotes so that the Pdx1 gene was disrupted to obtain Pdx1$^{+/mu}$ apancreatic rats (4 rats from the 3 ng/µl injection group and 3 rats from the 10 ng/µl injection group).

Among the obtained Pdx1 mutants, mutants A to D having four types of Pdx1 genes were found, as shown in FIG. 1B. The mutants A and B (hereinafter, referred to as "Pdx1$^{+/muA}$" and "Pdx1$^{+/muB}$", respectively) were frameshift mutants with stop codons corresponding to the 30th and 28th amino acids, respectively. Rats having the mutant A were mated with rats having the mutants B to obtain rats having the mutants A and B in their respective alleles (Pdx1$^{muA/muB}$). All the obtained rats exhibited an apancreatic phenotype (see FIG. 10) and died without 3 days after birth.

(2) Regeneration of Pancreas by Blastocyst Complementation

EGFP-labeled wild-type mouse iPS cells (GT3.2) or ESCs (mRHT or SGE2) were injected to a plurality of blastocysts obtained by mating Pdx1$^{+/muA}$ male rats with Pdx1$^{+/umB}$ female rats or mating Pdx1$^{+/muB}$ male rats with Pdx1$^{+/umA}$ female rats. The presence or absence of EGFP-negative peripheral blood mononuclear cells (PBMCs) was detected from PBMCs of the obtained 10-week-old rats. Rats having a Pdx1$^{muA/muB}$ genotype were confirmed with a frequency of 10% in the iPS cell injection group and with a frequency of 20% in the ES cell injection group. Since the rats die in 3 days after birth by the deletion of the pancreas, it was understood that the rats having a Pdx1$^{muA/muB}$ genotype were rats having the pancreas complemented by the iPS cells or the ES cells.

The pancreas formed in the rats having a Pdx1$^{muA/muB}$ genotype was observed to express EGFP as a whole. Specifically, the pancreas formed in the rats having a Pdx1$^{muA/muB}$ genotype was composed substantially of the mouse iPS cells or ES cells. Hereinafter, the pancreas formed in the rats having a Pdx1$^{muA/muB}$ genotype is referred to as "mouse $^R$pancreas". The formed mouse $^R$pancreas had the same size as that of the pancreas of a wild-type rat of the same age in weeks. Specifically, rat-sized large pancreas was obtained from cells of a mouse having a small body. In a glucose tolerance test (a 50% D-glucose solution was administered at 2.5 g/kg body weight), response to glucose was slow in the blastocyst-complemented Pdx1$^{muA/muB}$ rats compared with a Pdx1$^{+/mu}$ chimeric rat or a wild-type rat (p=0.035 vs. WT after 60 minutes from glucose administration; p=0.025 vs. WT after 120 minutes therefrom), whereas the glucose concentration was decreased to <200 mg/dL in 120 minutes from glucose administration. This demonstrated that the mouse $^R$pancreas functions in the rat body.

Example 2: Detection of Immune Rejection and Inflammation

In allogeneic pancreas transplantation, 50 to 70% of the pancreatic islet is disrupted due to immune rejection from immediately after the transplantation. Accordingly, the presence or absence of immune rejection was observed in the Pdx1$^{muA/muB}$ rats having the mouse $^R$pancreas prepared in Example 1.

Marked disruption of the pancreatic islet was not observed in the Pdx1$^{muA/muB}$ rats having the mouse $^R$pancreas. However, an abnormality occurred as the rats grew. A noticeable abnormality was observed in some rats, which developed polyuria and ketonuria (which are known as signs of diabetes mellitus).

Accordingly, the Pdx1$^{muA/muB}$ rats having the mouse $^R$pancreas, which manifested an abnormality, were subjected to a glucose tolerance test at 6 weeks and 10 weeks of age. The results were as shown in FIG. 2. As shown in FIG. 2, Pdx1$^{muA/muB}$ rat A having the mouse $^R$pancreas (Pdx1$^{muA/muB}$ rat-mouse chimeric individual A) obtained by blastocyst complementation had a normal fasting blood glucose level (95 mg/dL) at 6 weeks of age and exhibited response of the same level as that of a rat manifesting no sign of diabetes mellitus in the glucose tolerance test. However, this rat A manifested a sign of diabetes mellitus at 10 weeks of age and had a fasting blood glucose level of 252 mg/dL where the glucose response was no longer observed.

The pancreas of the rat that developed diabetes mellitus was histologically analyzed. As a result of staining sections of the pancreas with hematoxylin-eosin, the infiltration of lymphocytes was observed in the mouse $^R$pancreas (arrows in the lower right diagram of FIG. 2), and the presence was observed mainly in the accumulation part and also in nearby tissues including the pancreatic islet. The pancreatic islet (IL in the lower right diagram of FIG. 2) of the mouse $^R$pancreas was structurally destroyed by the attack of the lymphocytes.

Also, the infiltration of T cells and the infiltration of macrophages in the mouse $^R$pancreas were confirmed by immunohistological staining. The T cells were observed after reaction and staining of an anti-CD3 antibody as a primary antibody with a horseradish peroxidase-labeled secondary antibody. The macrophages were observed by similar staining using an anti-CD11b antibody as a primary antibody. The other procedures of the immunohistological staining were performed according to a routine method. The results were as shown in FIG. 3. As shown in FIG. 3, the infiltration of lymphocytes and macrophages in the pancreas (particularly, acinar cells and pancreatic islet) was observed (indicated by arrows). This indicates that the pancreas was attacked by immunity from the host so that inflammation occurred.

The xenogeneic chimeric animal individuals prepared by blastocyst complementation did not cause such inflammatory response in the mother body. Also, the inflammatory response described above was not a phenomenon observed in all xenogeneic chimeric animal individuals and occurred in some xenogeneic chimeric animal individuals.

This suggested that normal xenogeneic pancreas is also obtainable in such some individuals by at least suppressing inflammation with an anti-inflammatory agent.

Figure 4:
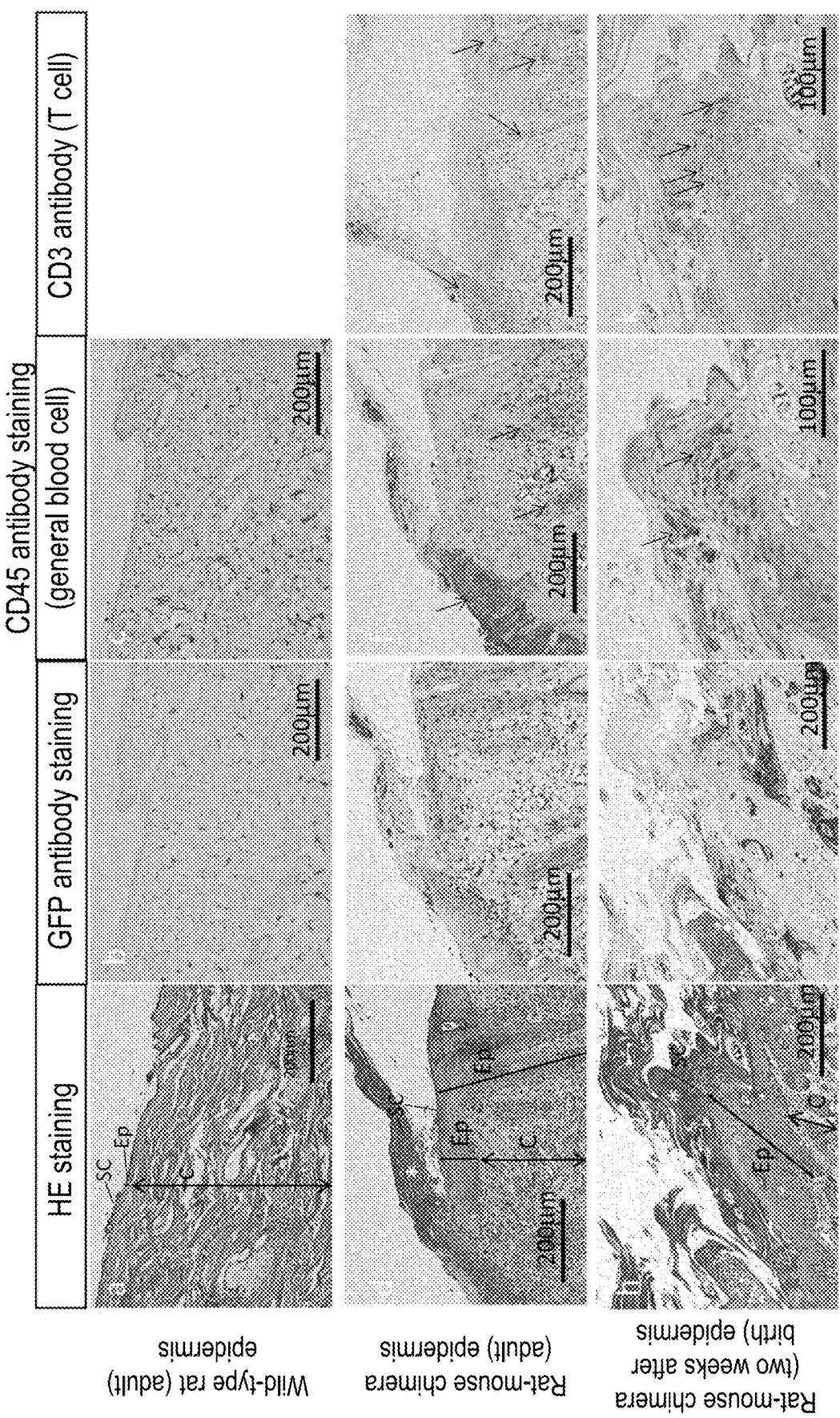
FIG. 4 is a view showing that blood cells containing T cells are accumulated at sites showing skin inflammation such as keratin thickening and skin loss occurring in a rat-mouse chimeric animal.

In the xenogeneic chimeric animal individuals prepared by blastocyst complementation, inflammation also occurred in the epidermis after birth. Hematoxylin-eosin staining produced the abnormal finding of epidermal thickening ("Ep" in FIGS. 4d and 4h) and stratum corneum thickening and desquamation ("*" in FIGS. 4d and 4h) in the mouse-rat chimeras prepared by transplanting mouse ES cells to rat embryos. More detailed analysis was further pursued by immunostaining. As a result of confirming the distribution of transplanted cell-derived cells on the basis of GFP, mouse ES cell-derived cells were found to exist in the region where the abnormal finding about the skin was gained (FIGS. 4e and 4i). The transplanted mouse ES cells were labeled with GFP and therefore stained according to a routine method through reaction with an anti-GFP antibody as a primary antibody and subsequent reaction with a HRP-labeled secondary antibody. As a result of similarly staining blood cells using an anti-CD45 antibody as a primary antibody, the accumulation of the blood cells was observed in the region where the abnormal finding was gained (FIGS. 4f and 4j). As a result of further staining T cells using an anti-CD3 antibody as a primary antibody, the accumulated blood cells were confirmed to include T cells (FIGS. 4g and 4k). These results showed that immune response or inflammatory response was also caused in the skin, as in the mouse $^R$pancreas shown in FIGS. 2 and 3. Accordingly, a steroid agent (Dermovate Ointment 0.05%, GlaxoSmithKline K.K.) was applied to the skin from 1 day after birth. As a result, the skin abnormality as indicated by arrows in an untreated group was no longer observed (see FIG. 5). These results demonstrated that inflammation in the pancreas can also be treated or prevented by the administration of an anti-inflammatory agent.

Example 3: Preparation of Xenogeneic Chimera Using Immunodeficient Animal

In this Example, immunodeficient animals were first prepared by the disruption of IL2Rg in order to obtain blastocysts of the immunodeficient animals. The phenotype of the IL2Rg−/− animals was confirmed, and xenogeneic chimeras were then prepared using blastocysts of the IL2Rg−/− animals.

(1) Preparation of IL2Rg−/− Rat

Figure 6A:
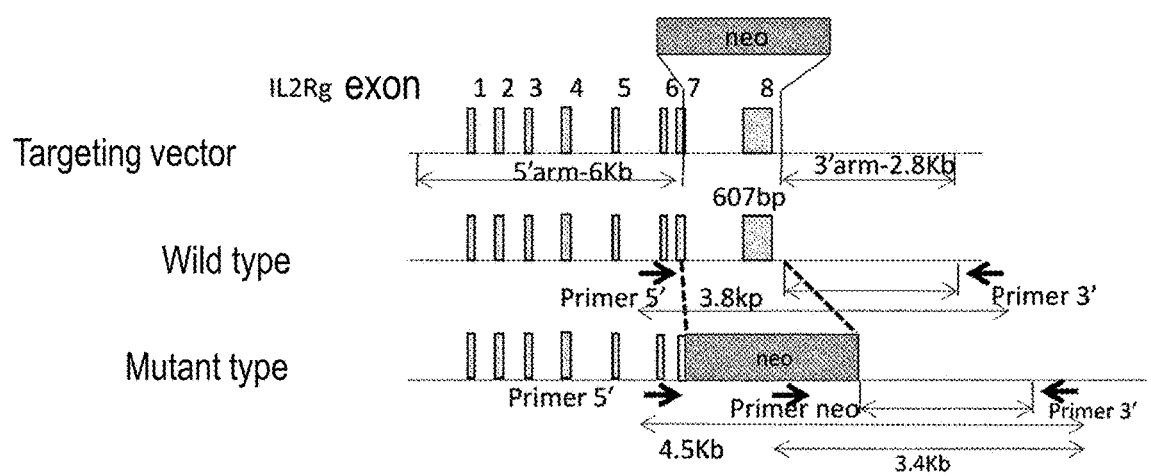
FIG. 6A is a diagram showing the structures of a targeting vector for preparing IL2Rg gene-disrupted animals and a disrupted gene.

The IL2Rg gene encodes interleukin 2 receptor γ subunit. In this Example, IL2Rg-disrupted rats were prepared by partially replacing exons of the IL2Rg gene with neomycin as a drug resistance gene using a targeting vector, as shown in FIG. 6A. Rat ES cells that received homologous recombination with the targeting vector were transplanted to rat pre-implantation embryos. The obtained chimeric rats were mated with wild-type rats to prepare IL2Rg+/− rats. Then, the IL2Rg+/− rats were mated with each other to obtain IL2Rg−/− rats in which the IL2Rg gene was disrupted.

(2) Phenotype of IL2Rg−/− Rat

Figure 6B:
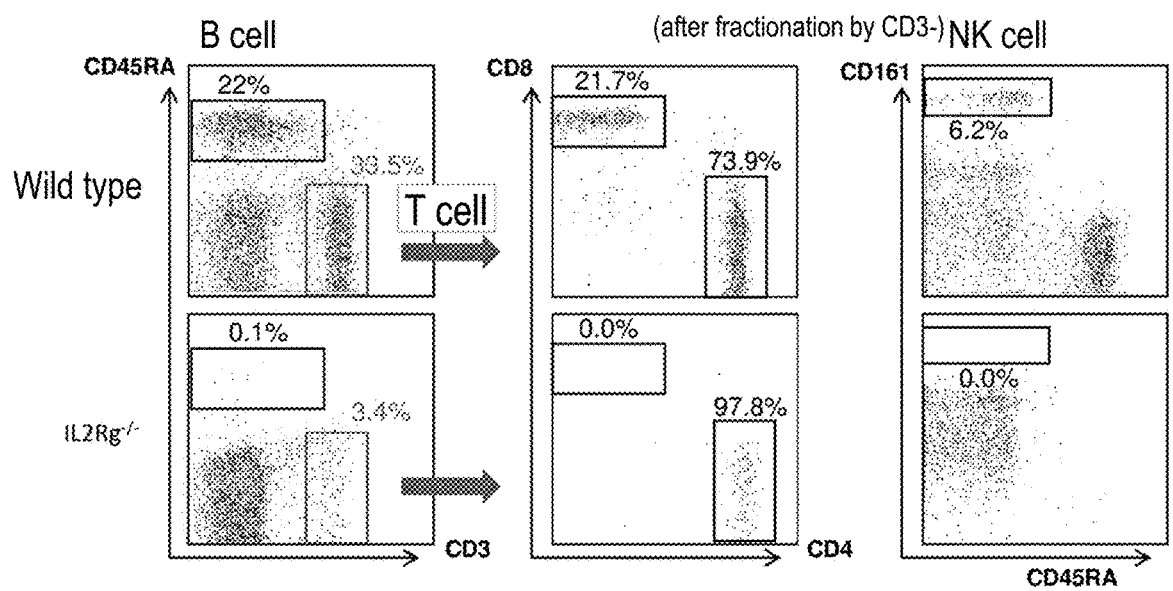
FIG. 6B shows results of blood cell analysis by flow cytometry on the peripheral blood of IL2Rg−/− rats.

Peripheral blood was collected from the obtained IL2Rg−/− rats, and blood cell fractions were observed by flow cytometry. The results were as shown in FIG. 6B. As shown in FIG. 6B, CD45R-positive and CD3-negative B cells were noticeably decreased in the IL2Rg−/− rats compared with a wild-type rat. Also, as shown in FIG. 6B, CD45R-negative and CD3-positive T cells were noticeably decreased from 33.5% (wild type) to 3.4% in the IL2Rg−/− rats. In addition, when the decreased T cells were further sorted, most of remaining T cells were CD4 single positive cells, whereas most of CD8 single positive cells disappeared. Furthermore, as shown in FIG. 6B, when the CD3-negative fractions of peripheral blood were sorted with CD45R and CD161, CD45R-negative and CD161-positive NK cells were noticeably decreased, as compared with a wild-type rat. Thus, immunocytes such as B cells, CD8 single positive cells and NK cells were noticeably decreased in the IL2Rg−/− rats compared with wild type.

Figure 6C:
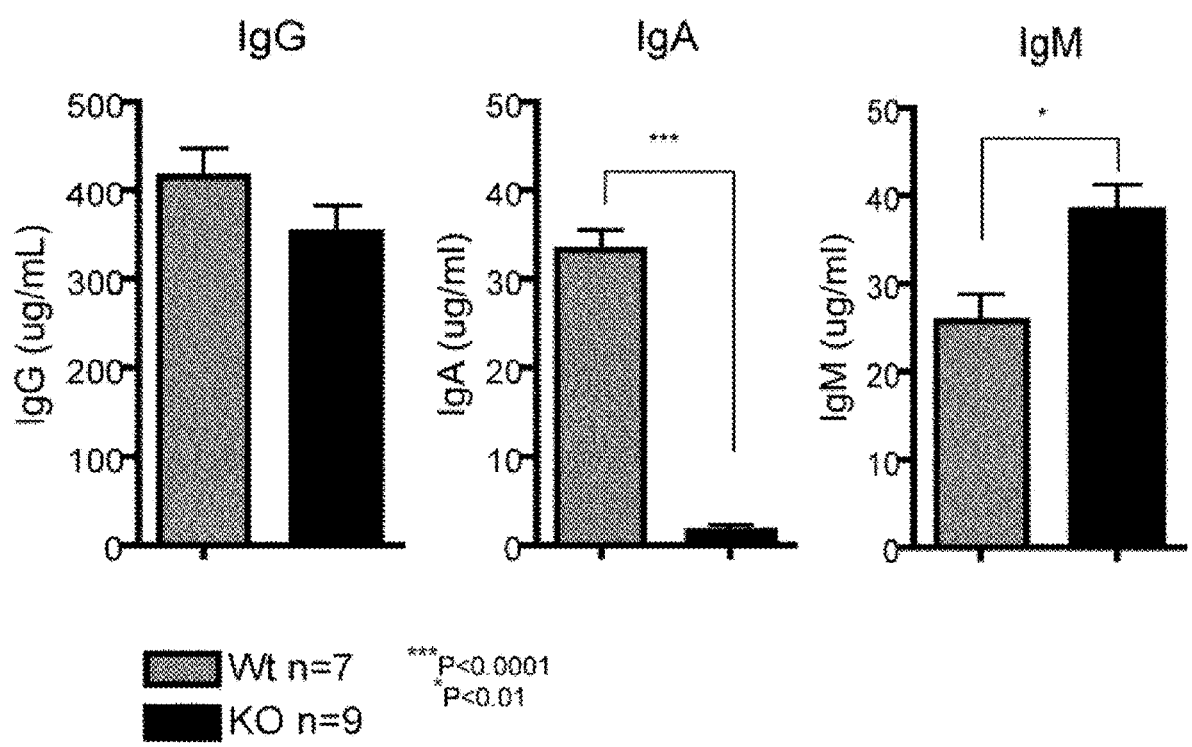
FIG. 6C shows the amounts of immunoglobulins in the peripheral blood of IL2Rg−/− rats.

The amounts of immunoglobulins in the blood of the IL2Rg−/− rats were analyzed according to a routine method. The results were as shown in FIG. 6C. The amount of IgG in the blood was equivalent between the IL2Rg−/− rats and a wild-type rat, whereas the amount of IgA in the blood was noticeably decreased in the IL2Rg−/− rats. This suggested that cell-mediated immunity was strongly suppressed in the IL2Rg−/− rats.

(3) Preparation and Analysis of Rat-Mouse Chimeric Animal Using IL2Rg−/− Rat Embryo In the same way as in the preceding Example, wild-type mouse ES cells were transplanted to pre-implantation embryos of the IL2Rg−/− rats to prepare xenogeneic chimeric animals (referred to as IL2Rg−/− rat-mouse chimeras). Xenogeneic chimeric animals obtained by transplanting wild-type mouse ES cells to pre-implantation embryos of wild-type rats (referred to as wild-type rat-mouse chimeras) were used as controls. Next, the peripheral blood of the IL2Rg−/− rat-mouse chimeras was recovered, and blood cell fractions were obtained by flow cytometry. The results were as shown in FIG. 7A. As shown in FIG. 7A, both rat-derived and mouse-derived T cells, B cells and NK cells were observed in the wild-type rat-mouse chimeras. By contrast, mouse-derived T cells, B cells and NK cells were observed in the IL2Rg−/− rat-mouse chimeras, whereas rat-derived T cells, B cells and NK cells were noticeably decreased therein. Thus, immunocytes derived from the blastocysts in which the IL2Rg gene was disrupted were noticeably decreased in the IL2Rg−/− rat-mouse chimeras.

Figure 7B:
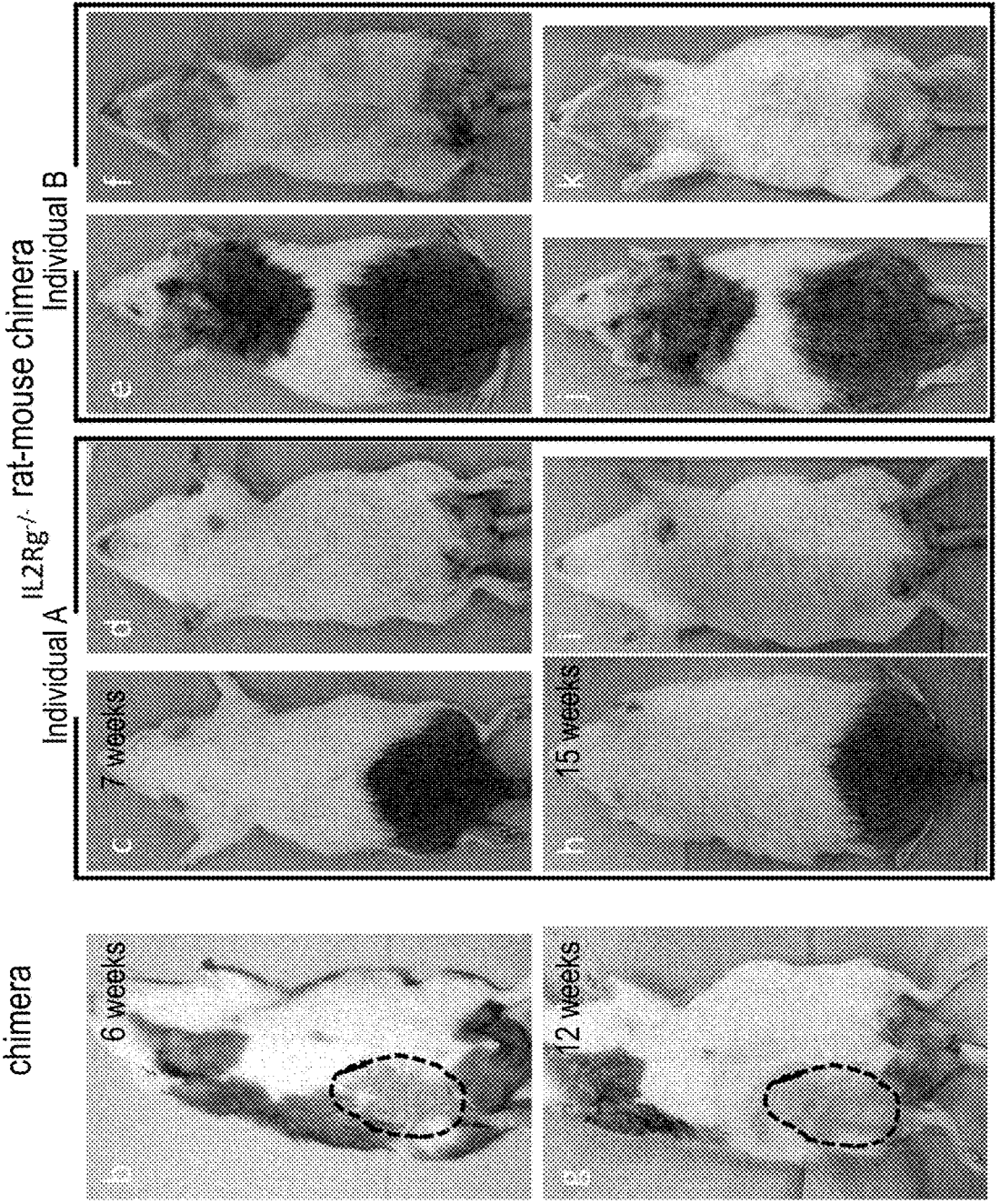
FIG. 7B shows the state of inflammation in the epidermis of IL2Rg−/− rat-mouse chimeras.

Next, the epidermis of the IL2Rg−/− rat-mouse chimeras was observed. The results were as shown in FIG. 7B. Panel b of FIG. 7B shows an image of epidermal inflammation common in the wild-type rat-mouse chimeras (6 weeks old). Panel g of FIG. 7B shows an image of epidermal inflammation common in the wild-type rat-mouse chimeras (12 weeks old). Panels c and d of FIG. 7B show the dorsal and ventral sides, respectively, of the IL2Rg−/− rat-mouse chimera (7 weeks old). Panels h and i of FIG. 7B show the dorsal and ventral sides, respectively, of the IL2Rg−/− rat-mouse chimera (12 weeks old). Epidermal inflammation or alopecia observed in the wild type was not observed in the IL2Rg−/− rat-mouse chimera. Although epidermal inflammation was confirmed in another individual of the IL2Rg−/− rat-mouse chimera, no particular epidermal inflammation was confirmed, as in the chimera described above. Panels e and f of FIG. 7B show the dorsal and ventral sides, respectively, of another individual (7 weeks old) of the IL2Rg−/− rat-mouse chimera. Panels j and k of FIG. 7B show the dorsal and ventral sides, respectively, of the IL2Rg−/− rat-mouse chimera (12 weeks old).

Tissue sections were further prepared from the skin of the IL2Rg−/− rat-mouse chimeras according to a routine method and histologically analyzed. The results were as shown in FIG. 7C. The thickening of the epithelial layer and the dermic layer was confirmed in the skin of the wild-type rat-mouse chimera shown in panel m of FIG. 7C and panel p which is a high magnification image thereof, as compared with the skin of a wild-type rat shown in panel l of FIG. 7C and panel o which is a high magnification image thereof. This thickening of the epithelial layer and the dermic layer was considered to be ascribable to inflammation. By contrast, the thickening of skin tissues was not observed in the IL2Rg−/− rat-mouse chimera shown in panel n of FIG. 7C and panel q which is a high magnification image thereof. Abnormal keratinization (increased keratinization) of the skin was observed in the wild-type rat-mouse chimeras, whereas this abnormal keratinization was not suppressed in the IL2Rg−/− rat-mouse chimeras.

(4) Preparation and Analysis of Rat-Mouse Chimeric Animal Using IL2Rg−/− Mouse ES Cell The IL2Rg gene in mouse ES cells was disrupted by the CRISPR/Cas9 method to obtain IL2Rg−/− mouse ES cells. The obtained IL2Rg−/− mouse ES cells were transplanted to pre-implantation embryos of wild-type rats to prepare xenogeneic chimeras. The epidermis of the obtained xenogeneic chimeras was observed on 1 day and 7 days after birth. The results were as shown in panels a to d of FIG. 8A. As shown in panels b to d of FIG. 8A, abnormal keratinization (increased keratinization) or skin thickening was observed in the epidermis of this xenogeneic chimera.

(5) Influence of Disruption of Immune System in Both ES Cell and Embryo

Accordingly, IL2Rg−/− mouse ES cells were introduced to pre-implantation embryos of IL2Rg−/− rats to prepare xenogeneic chimeras in which T cells, B cells and NK cells were noticeably decreased or eliminated. The epidermis of the obtained xenogeneic chimeras was observed on 1 day and 7 days after birth. The results were as shown in panels e and f of FIG. 8A. As shown in panels e and f of FIG. 8A, the abnormal keratinization or the thickening described above was not observed in the skin of the xenogeneic chimeric animals derived from the ES cells and the embryos, both of which were IL2Rg gene-disrupted. No epidermal inflammatory response was observed around 6 weeks after birth of the xenogeneic chimeric animals derived from the ES cells and the embryos, both of which were IL2Rg gene-disrupted.

Figure 8B:
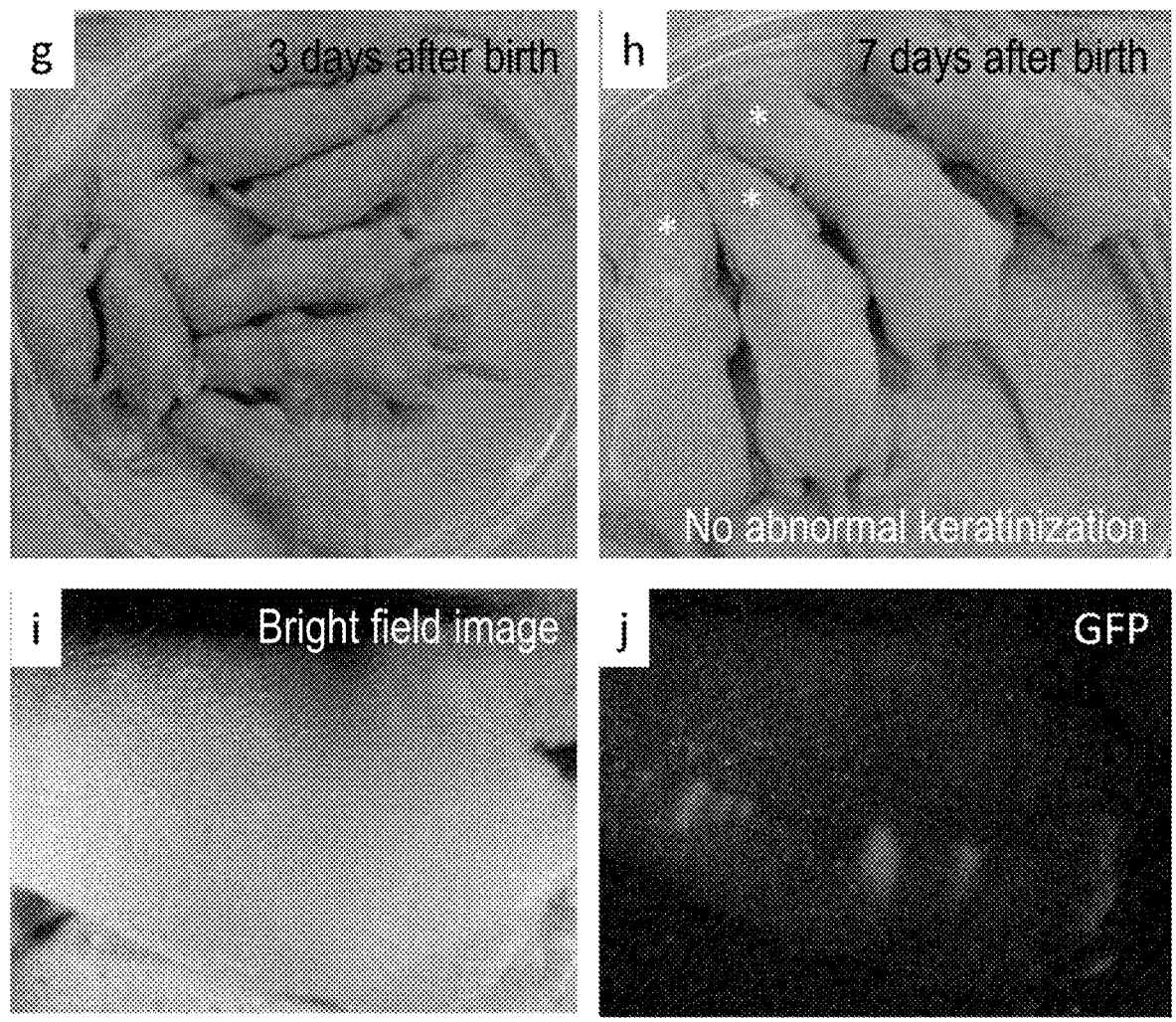
FIG. 8B shows the state of the epidermis in rat-mouse chimeric animals prepared from NSG mouse ES cells and IL2Rg−/− Rag2−/− rat embryos (panels g to j).

Next, ES cells of NSG mice (NOD.Cg-Prkdc$^{scid}$Il2rg$^{tm1Wjl}$/SzJ) were introduced to pre-implantation embryos of IL2Rg−/− RAG2−/− rats to prepare xenogeneic chimeras in which the immune system was severely disrupted. The NSG mice are known as severely immunodeficient mice, and the IL2Rg−/− RAG2−/− rats also manifest severe immunodeficiency. Chimeric individuals were identified on the basis of GFP forcedly expressed in the NSG mouse ES cells. When this xenogeneic chimeric animal in which the immune system was severely disrupted was observed under a fluorescence microscope, xenogeneic chimeric individuals having mouse cells expressing GFP and rat cells expressing no GFP were obtained as shown in panel j of FIG. 8B. As a result of observing the epidermis on 7 days after birth in such xenogeneic chimeric animals, neither abnormal keratinization nor thickening was observed in the skin. No epidermal inflammatory response was observed around 6 weeks after birth of this xenogeneic chimeric animal. In FIG. 8B, animals marked with "*" in their heads were xenogeneic chimeric individuals, whereas animals without the mark "*" were non-chimeric litters. The results described above showing that the NSG mice more strongly suffered from decreased functions of the acquired immune system and the innate immune system, and the abnormality was more strongly suppressed by the transplantation of NSG mouse-derived ES cells, suggest that the acquired immune system and the innate immune system are involved in the inflammation or the immune response. The acquired immune system was strongly suppressed in the NSG animals or the IL2Rg−/− RAG2−/− animals compared with IL2Rg−/− animals, whereas the inflammation or the immune response was more strongly suppressed in an experiment combining NSG and IL2Rg−/− RAG2−/− than in the IL2Rg−/− animals, also suggesting that the acquired immune system is involved in the inflammation or the immune response.

Thus, it was confirmed that inflammation or abnormal immunity in xenogeneic chimeric individuals is reduced by suppressing the immunity or the inflammation.

SEQUENCE LISTING

SEQ ID NO: 1: Target sequence (left) of TALEN in exon 1 of the rat Pdx1 gene
SEQ ID NO: 2: Target sequence (right) of TALEN in exon 1 of the rat Pdx1 gene
SEQ ID NO: 3: Wild-type sequence of the target portion in the rat Pdx1 gene
SEQ ID NO: 4: Modified sequence of the target portion in the rat Pdx1 gene (mutant A)
SEQ ID NO: 5: Modified sequence of the target portion in the rat Pdx1 gene (mutant B)
SEQ ID NO: 6: Modified sequence of the target portion in the rat Pdx1 gene (mutant C)
SEQ ID NO: 7: Modified sequence of the target portion in the rat Pdx1 gene (mutant D)

The invention claimed is:

1. A method for obtaining an adult individual from a xenogeneic or allogeneic chimeric animal fetus individual, the method comprising:
provides a xenogeneic or allogeneic chimeric animal fetus individual that shows no substantial inflammation;
obtaining an adult individual from the fetus individual by growing the fetus individual; and
administering an effective amount of an anti-inflammatory agent or an immunosuppressive agent to the individual before the birth of the individual and/or after the birth, wherein the effective amount is sufficient to suppress inflammation after the birth of the individual.

2. The method according to claim 1, wherein the anti-inflammatory agent or the immunosuppressive agent is administered before occurrence of immune response or inflammation in the individual.

3. The method according to claim 1, further comprising:
confirming that the immune response or the inflammation has occurred in the epidermis of the born individual; and
administering the anti-inflammatory agent or the immunosuppressive agent to the individual thus confirmed to have the immune response or the inflammation.

4. The method according to claim 1, wherein the individual induces inflammation after its birth.

5. The method according to claim 1, wherein the individual is immunodeficient.

6. The method according to claim 5, wherein the immunodeficiency is associated with a genetic modification or an abnormality in any one or more members selected from Interleukin 2 receptor subunit gamma (IL2Rg), recombination-activating gene 1 (RAG1), recombination-activating gene 2 (RAG2), forkhead box protein N1 (Foxn1), protein kinase, DNA-activated, catalytic subunit (PRKDC), major histocompatibility complex (MHC) and signal-regulatory protein alpha (SIRPa).

7. The method according to claim 2, wherein the individual induces inflammation after its birth.

8. The method according to claim 2, wherein the individual is immunodeficient.

9. The method according to claim 8, wherein the immunodeficiency is associated with a genetic modification or an abnormality in any one or more members selected from Interleukin 2 receptor subunit gamma (IL2Rg), recombination-activating gene 1 (RAG1), recombination-activating gene 2 (RAG2), forkhead box protein N1 (Foxn1), protein kinase, DNA-activated, catalytic subunit (PRKDC), major histocompatibility complex (MHC) and signal-regulatory protein alpha (SIRPa).

10. The method according to claim 3, wherein the individual induces inflammation after its birth.

11. The method according to claim 3, wherein the individual is immunodeficient.

12. The method according to claim 11, wherein the immunodeficiency is associated with a genetic modification or an abnormality in any one or more members selected from Interleukin 2 receptor subunit gamma (IL2Rg), recombination-activating gene 1 (RAG1), recombination-activating gene 2 (RAG2), forkhead box protein N1 (Foxn1), protein kinase, DNA-activated, catalytic subunit (PRKDC), major histocompatibility complex (MHC) and signal-regulatory protein alpha (SIRPa).

* * * * *

SEQUENCE LISTING

<160> NUMBER OF SEQ ID NOS: 7

<210> SEQ ID NO 1
<211> LENGTH: 17
<212> TYPE: DNA

-continued

```
<213> ORGANISM: Artificial Sequence
<220> FEATURE:
<223> OTHER INFORMATION: Synthetic Construct

<400> SEQUENCE: 1
tagtgaggag cagtact                                                    17

<210> SEQ ID NO 2
<211> LENGTH: 17
<212> TYPE: DNA
<213> ORGANISM: Artificial Sequence
<220> FEATURE:
<223> OTHER INFORMATION: Synthetic Construct

<400> SEQUENCE: 2
tctacaagga cccgtgc                                                    17

<210> SEQ ID NO 3
<211> LENGTH: 57
<212> TYPE: DNA
<213> ORGANISM: Artificial Sequence
<220> FEATURE:
<223> OTHER INFORMATION: Synthetic Construct

<400> SEQUENCE: 3
atgaatagtg aggagcagta ctacgcggcc acacagctct acaaggaccc gtgcgca       57

<210> SEQ ID NO 4
<211> LENGTH: 55
<212> TYPE: DNA
<213> ORGANISM: Artificial Sequence
<220> FEATURE:
<223> OTHER INFORMATION: Synthetic Construct

<400> SEQUENCE: 4
atgaatagtg aggagcagta ctacgcggcc acagctctac aaggacccgt gcgca         55

<210> SEQ ID NO 5
<211> LENGTH: 49
<212> TYPE: DNA
<213> ORGANISM: Artificial Sequence
<220> FEATURE:
<223> OTHER INFORMATION: Synthetic Construct

<400> SEQUENCE: 5
atgaatagtg aggagcagta ctacgcggct ctacaaggac ccgtgcgca                49

<210> SEQ ID NO 6
<211> LENGTH: 48
<212> TYPE: DNA
<213> ORGANISM: Artificial Sequence
<220> FEATURE:
<223> OTHER INFORMATION: Synthetic Construct

<400> SEQUENCE: 6
atgaatagtg aggagcagta ctacgcgctc tacaaggacc cgtgcgca                 48

<210> SEQ ID NO 7
<211> LENGTH: 49
<212> TYPE: DNA
<213> ORGANISM: Artificial Sequence
<220> FEATURE:
```

```
<223> OTHER INFORMATION: Synthetic Construct

<400> SEQUENCE: 7
atgaatagtg aggagcagta tacgcgggct ctacaaggac ccgtgcgca                49
```